(12) United States Patent
Hoye et al.

(10) Patent No.: US 9,375,484 B2
(45) Date of Patent: Jun. 28, 2016

(54) TAXANE SILICATE PRODRUGS AND NANOPARTICLES

(75) Inventors: Thomas R. Hoye, St. Paul, MN (US); Adam Wohl, St. Paul, MN (US); Christopher W. Macosko, St. Paul, MN (US); Jayanth Panyam, St. Paul, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 14/123,448

(22) PCT Filed: May 31, 2012

(86) PCT No.: PCT/US2012/040247
§ 371 (c)(1),
(2), (4) Date: Feb. 28, 2014

(87) PCT Pub. No.: WO2012/166949
PCT Pub. Date: Dec. 6, 2012

(65) Prior Publication Data
US 2014/0213550 A1    Jul. 31, 2014

Related U.S. Application Data

(60) Provisional application No. 61/491,773, filed on May 31, 2011.

(51) Int. Cl.
*A61K 31/695* (2006.01)
*A61K 9/19* (2006.01)
(Continued)

(52) U.S. Cl.
CPC .......... *A61K 47/48023* (2013.01); *A61K 9/0019* (2013.01); *A61K 9/5153* (2013.01); *A61K 31/695* (2013.01); *C07F 7/045* (2013.01); *A61K 9/19* (2013.01)

(58) Field of Classification Search
CPC ............... C07D 305/14; C07D 305/06; A61K 47/48023; A61K 31/695; A61K 9/0019; A61K 9/19; A61K 9/5153; C07F 7/045
USPC .................................................. 549/510, 511
See application file for complete search history.

(56) References Cited

U.S. PATENT DOCUMENTS

| 6,242,614 B1 * | 6/2001 | Vemishetti ........... C07D 305/14 |
| | | 549/214 |
| 8,252,337 B2 * | 8/2012 | Lee et al. ....................... 424/489 |

(Continued)

FOREIGN PATENT DOCUMENTS

| WO | WO 00/38655 A1 | 7/2000 |
| WO | WO 2009/141738 A2 | 11/2009 |

OTHER PUBLICATIONS

Han, et al., "Block Copolymer Protected Nanoparticles and drug release study for Cancer Therapy", Poster, IPRIME Annual Meeting, Jun. 1, 2011.

(Continued)

*Primary Examiner* — Valerie Rodriguez-Garcia
(74) *Attorney, Agent, or Firm* — Viksnins Harris & Padys PLLP

(57) ABSTRACT

The invention provides silicate prodrugs comprising a therapeutic agent linked to one or more groups of formula (I): —Si(OR)$_3$ (I); wherein each R independently has any of the values defined herein, as well as nanoparticles comprising such compounds.

35 Claims, 5 Drawing Sheets

Synthesis of the silicate prodrugs of PTX. Conditions: (a) SiCl(OR$^1$)$_3$, NEt$_3$, THF. (b) i) SiCl$_2$(O$^t$Bu)$_2$, py, THF; ii) EtOH, py. (c) SiCl(OR)$_3$, py, THF. (d) d$_6$-acetone, D$_2$O, TFA (90:9:1 v/v/v). Yields of chromatographed product: 1a (91%); 1b (81%); 1c (65%); 1d (84%); 2a (85%); 2b (77%); 3a (91%, brsm); and 3b (66%, brsm). brsm = based on recovered starting material.

(51) Int. Cl.
- *C07D 305/14* (2006.01)
- *A61K 31/337* (2006.01)
- *A61K 47/48* (2006.01)
- *A61K 9/00* (2006.01)
- *A61K 9/51* (2006.01)
- *C07F 7/04* (2006.01)

(56) References Cited

U.S. PATENT DOCUMENTS

| | | | |
|---|---|---|---|
| 8,304,392 B2* | 11/2012 | Dal Farra et al. | 514/21.8 |
| 8,545,877 B2* | 10/2013 | Cullis et al. | 424/450 |
| 2009/0124680 A1* | 5/2009 | Yoo | A61K 31/4178 514/397 |
| 2010/0104650 A1 | 4/2010 | Lee et al. | |
| 2011/0123446 A1 | 5/2011 | Desimone et al. | |

OTHER PUBLICATIONS

Han, "Block Copolymer Protected Nanoparticles and Drug Release Study for Cancer Therapy", Poster, 6th Annual Minnesota Nanotechnology Conference, Minneapolis, MN, 1 page, Oct. 2010.

Hoye et al., "PCL-b-PEG Nanoparticles for Drug Delivery: Package and Contents", IPRIME Annual Meeting, Minneapolis, MN, 56 pages, May 31, 2007.

Johnson et al., "Chemical Processing and Micromixing in Confined Impinging Jets", *AIChE Journal*, vol. 49 (9), 2264-2282 (2003).

Johnson et al., "Flash NanoPrecipitation of Organic Actives and Block Copolymers using a Confined Impinging Jets Mixer", *Aust. J. Chem.* 56, 1021-1024 (2003).

Macosko, "Polymer Protected Nanoparticles for Drug Delivery", Presentation, IIT-Mumbai, 33 pages, Feb. 27, 2009.

Michel et al., "PEG-b-PLGA-Based Nanopanicle Delivery of a Silicate Prodrug: Tissue Distribution in Mice", Poster, IPrime, 1 page, Jun. 2011.

Patent Cooperation Treaty, International Searching Authority, Search Report and Written Opinion for PCT/US2012/40247, 10 pages, Sep. 26, 2012.

Wohl et al., "Silicate Prodrug-Loaded Block Copolymer Nanoparticles", IPRIME Poster, Jun. 2, 2010.

Wohl et al., "Silicate Prodrug-Loaded Nanoparticles", AIChE Annual Meeting, Minneapolis, MN, 60 pages, Oct. 17, 2011.

Wohl et al., "Silicate Prodrug-Loaded Block Copolymer Nanoparticles: Controlling Both the Cargo and the Packaging", IPRIME Annual Meeting, 44 pages, Jun. 1, 2011.

Wohl et al., "Silicate Prodrug-Loaded Block Copolymer Nanoparticles: Particle Formation, Silicate Hydrolysis, and Drug Release", AIChE Presentation, Salt Lake City, UT, 54 pages, Nov. 10, 2010.

Macosko, "Polymer Protected Nanoparticles for Drug Delivery", Presentation IIT-Mumbai, 29 pages Feb. 27, 2009.

\* cited by examiner

Synthesis of the silicate prodrugs of PTX. Conditions: (a) SiCl(OR$^1$)$_3$, NEt$_3$, THF. (b) i) SiCl$_2$(O$^t$Bu)$_2$, py, THF; ii) EtOH, py. (c) SiCl(OR)$_3$, py, THF. (d) d$_6$-acetone, D$_2$O, TFA (90:9:1 v/v/v). Yields of chromatographed product: 1a (91%); 1b (81%); 1c (65%); 1d (84%); 2a (85%); 2b (77%); 3a (91%, brsm); and 3b (66%, brsm). brsm = based on recovered starting material.

Mean luminescence quantitation. Photon intensity from the primary tumor site was determined for ≥4 mice at each time point. CrEL® and blank NP groups are shown up to the time point preceding euthanasia or death of a majority of the group. "x" indicates too few surviving animals for meaningful data interpretation. Data are presented as mean ±S.D.

TAXANE SILICATE PRODRUGS AND NANOPARTICLES

PRIORITY OF INVENTION

The application claims priority to U.S. Provisional Application No. 61/491,773, filed 31 May 2011. The entire content of this provisional application is hereby incorporated by reference herein.

STATEMENT OF GOVERNMENT RIGHTS

This invention was made with government support under EB011671 awarded by the National Institutes of Health. The government has certain rights in the invention.

BACKGROUND OF THE INVENTION

The use and effectiveness of many therapeutic agents is limited by the solubility of the agents. Taxanes like paclitaxel and docetaxel are chemotherapy agents that are commonly used in the treatment of breast, lung, prostate and other cancers. Taxanes interfere with the microtubules in the cancer cell, stopping the cell from dividing and causing its death. Unfortunately, the use and effectiveness of taxanes is limited by the solubility of the agents.

Taxol® and Taxotere®, two leading cancer therapeutics, are formulations of the minimally water-soluble antitumor agents paclitaxel (PTX) and docetaxel (DTX), respectively, solubilized in the adjuvants Cremophor EL® and polysorbate 80 (Tween 80®), respectively. However, Taxol® and Taxotere® contain only about 1 and 4 wt %, respectively, of the actives. The large amount of the surfactant/excipient/carrier that accompanies drug dosage leads to a range of undesirable side effects. For example, many patients show acute hypersensitivity response to Cremophor EL® present in Taxol®; 1.5-3% suffer major, potentially life-threatening reactions. Abraxane® is an alternative formulation of PTX in which a "human albumin-stabilized, lyophilized NP formulation" is used instead of Cremophor EL®. Abraxane® contains ca. 10 wt % PTX, and is approved only for second-line metastatic breast cancer patients. Clearly there is a need for developing improved formulations for taxane (and other similarly hydrophobic) antitumor agents.

There is currently a need for methods to modify the solubility of certain therapeutic agents to improve their ability to be administered as therapeutics. There is also a need for new formulations and for formulating methods that can be used to deliver therapeutic agents to patients. In particular, there is a need for formulations that have higher drug loading (i.e., less excipient), that can be localized preferentially at a tumor site, or that selectively release their drug payload in the environment (e.g. more acidic) of the tumor.

SUMMARY OF THE INVENTION

Applicant has discovered that silicate ester derivatives of drugs [e.g., DRUG-O—Si(OR)$_3$, wherein each R can be the same or different] can function as prodrugs. The silicate moiety can be tailored to dictate, independently, both the hydrophobicity of the prodrug as well as its rate of hydrolysis. Additionally, Applicant has discovered that these silicate prodrugs can be co-precipitated with biocompatible block copolymers (BCPs), using flash nanoprecipitation (FNP), to produce nanoparticles (NPs) in a size regime ideal for exploiting the enhanced permeation and retention (EPR) effect (e.g. about 100 nm diameter) for localization of particles at solid tumor sites.

Accordingly there is provided a compound of the invention which is a compound comprising a therapeutic agent linked to one or more (e.g. 1, 2, 3, or 4) groups of formula (I):

$$—Si(OR)_3 \qquad (I)$$

wherein:
each R is independently selected from $(C_1\text{-}C_{20})$alkyl, $(C_2\text{-}C_{20})$alkenyl, $(C_2\text{-}C_{20})$alkynyl, $(C_1\text{-}C_{20})$alkanoyl, $(C_2\text{-}C_{20})$alkenylcarbonyl, and $(C_2\text{-}C_{20})$alkynylcarbonyl, wherein each $(C_1\text{-}C_{20})$alkyl, $(C_2\text{-}C_{20})$alkenyl, $(C_2\text{-}C_{20})$alkynyl, $(C_1\text{-}C_{20})$alkanoyl, $(C_2\text{-}C_{20})$alkenylcarbonyl, and $(C_2\text{-}C_{20})$alkynylcarbonyl, is optionally substituted with one or more hydroxy, $(C_1\text{-}C_6)$alkoxy, oxo, halo, or aryl.

The invention also provides a formulation comprising a compound of the invention and a PEG-b-PLGA block copolymer.

The invention also provides a nano-particle comprising a compound of the invention and a PEG-b-PLGA block copolymer.

The invention also provides a method to treat cancer in an animal (e.g. a human) comprising administering a compound of the invention or a formulation of the invention to the animal.

The invention also provides a compound of the invention or a formulation of the invention for use in medical therapy.

The invention also provides a compound of the invention or a formulation of the invention for the prophylactic or therapeutic treatment of cancer.

The invention also provides the use of a compound of the invention or a formulation of the invention to prepare a medicament for treating cancer in an animal (e.g. a human).

The invention also provides processes and intermediates disclosed herein that are useful for preparing compounds or formulations of the invention.

The prodrugs and formulations of the invention have a number of useful advantages. For example, certain formulations of the invention have higher drug loading (e.g. less excipient), can be localized preferentially at a tumor site, or selectively release their drug payload in the environment (e.g. more acidic) of the tumor.

DETAILED DESCRIPTION

Figure 1:
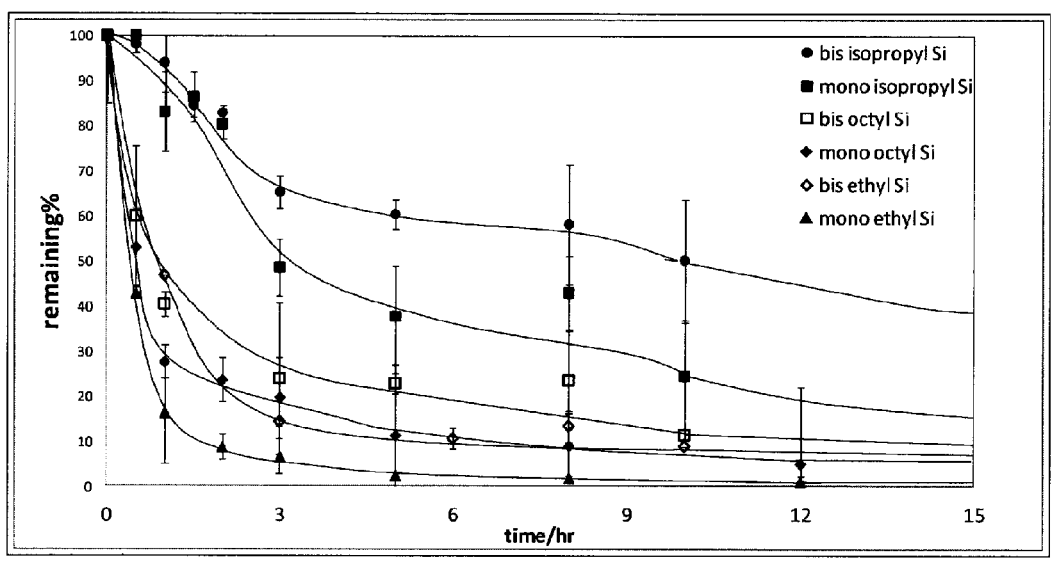
FIG. 1 Illustrates release data for representative compounds of formula (I) from Example 10.

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. $(C_2\text{-}C_{20})$Alkenyl is a $(C_2\text{-}C_{20})$alkyl chain having one or more double bonds in the chain. $(C_2\text{-}C_{20})$Alkynyl is a $(C_2\text{-}C_{20})$ alkyl chain having one or more triple bonds and optionally one or more double bonds in the chain. $(C_1-C_{20})$alkanoyl is $(C_1-C_{19})$alkylC(=O)—. $(C_2-C_{20})$Alkenylcarbonyl is $(C_2-C_{20})$alkenylC(=O)—. $(C_2-C_{20})$Alkynylcarbonyl is $(C_2-C_{20})$alkynylC(=O)—. Aryl denotes a phenyl radical or an ortho-fused bicyclic carbocyclic radical having about nine to ten ring atoms in which at least one ring is aromatic.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Specific values listed below for radicals, substituents, and ranges, are for illustration only; they do not exclude other defined values or other values within defined ranges for the radicals and substituents.

Specifically, $(C_1-C_{20})$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, iso-propoxy, butoxy, iso-butoxy, sec-butoxy, pentoxy, 3-pentoxy, or hexyloxy; $(C_2-C_{20})$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_{20})$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_{20})$alkanoyl can be acetyl, propanoyl or butanoyl; and aryl can be phenyl, indenyl, or naphthyl.

In one embodiment of the invention an oxygen of a hydroxy group of the therapeutic agent is linked to the group of formula (I).

In one embodiment of the invention each R is independently selected from $(C_{10}-C_{20})$alkyl, $(C_{10}-C_{20})$alkenyl, $(C_{10}-C_{20})$alkynyl, $(C_{10}-C_{20})$alkanoyl, $(C_{10}-C_{20})$alkenylcarbonyl, $(C_{10}-C_{20})$alkynylcarbonyl, wherein each $(C_{10}-C_{20})$alkyl, $(C_{10}-C_{20})$alkenyl, $(C_{10}-C_{20})$alkynyl, $(C_{10}-C_{20})$alkanoyl, $(C_{10}-C_{20})$alkenylcarbonyl, $(C_{10}-C_{20})$alkynylcarbonyl, is optionally substituted with one or more hydroxy, $(C_1-C_6)$alkoxy, oxo, halo, or aryl.

In one embodiment of the invention each R is independently selected from $(C_5-C_{20})$alkyl, $(C_5-C_{20})$alkenyl, $(C_5-C_{20})$alkynyl, $(C_5-C_{20})$alkanoyl, $(C_5-C_{20})$alkenylcarbonyl, $(C_5-C_{20})$alkynylcarbonyl, wherein each $(C_5-C_{20})$alkyl, $(C_5-C_{20})$alkenyl, $(C_5-C_{20})$alkynyl, $(C_5-C_{20})$alkanoyl, $(C_5-C_{20})$alkenylcarbonyl, $(C_5-C_{20})$alkynylcarbonyl, is optionally substituted with one or more hydroxy, $(C_1-C_6)$alkoxy, oxo, halo, or aryl.

In one embodiment of the invention oxygens of at least two (e.g. 1, 2, or 3) hydroxy groups of the therapeutic agent are linked to groups of formula (I).

In one embodiment of the invention each R is independently selected from $(C_1-C_{20})$alkyl, $(C_2-C_{20})$alkenyl, and $(C_2-C_{20})$alkynyl, wherein each $(C_1-C_{20})$alkyl, $(C_2-C_{20})$alkenyl, and $(C_2-C_{20})$alkynyl is optionally substituted with one or more hydroxy, $(C_1-C_6)$alkoxy, oxo, halo, or aryl.

In one embodiment of the invention each R is independently selected from $(C_1-C_{20})$alkanoyl, $(C_2-C_{20})$alkenylcarbonyl, $(C_2-C_{20})$alkynylcarbonyl, wherein each $(C_1-C_{20})$alkanoyl, $(C_2-C_{20})$alkenylcarbonyl, $(C_2-C_{20})$alkynylcarbonyl, is optionally substituted with one or more hydroxy, $(C_1-C_6)$alkoxy, oxo, halo, or aryl.

In one embodiment of the invention at least one R is independently selected from $(C_1-C_{20})$alkanoyl, $(C_2-C_{20})$alkenylcarbonyl, $(C_2-C_{20})$alkynylcarbonyl, wherein each $(C_1-C_{20})$alkanoyl, $(C_2-C_{20})$alkenylcarbonyl, $(C_2-C_{20})$alkynylcarbonyl, is optionally substituted with one or more hydroxy, $(C_1-C_6)$alkoxy, oxo, halo, or aryl.

In one embodiment of the invention the therapeutic agent is a taxane.

In one embodiment of the invention the therapeutic agent is a paclitaxel or docetaxel.

In one embodiment the invention provides a compound of formula (Ia):

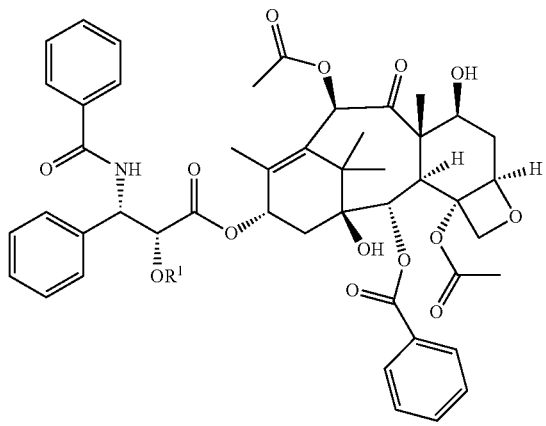

(Ia)

wherein $R^1$ is a group of formula (I), or a salt thereof.

In one embodiment of the invention provides a compound of formula (Ib):

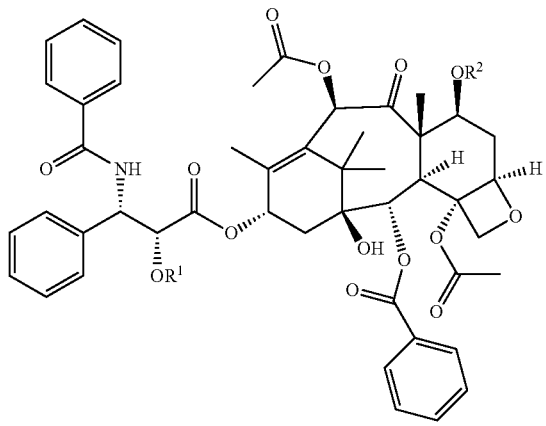

(Ib)

wherein $R^1$ and $R^2$ are each independently a group of formula (I), or a salt thereof.

In one embodiment of the invention provides a compound of formula (Ic):
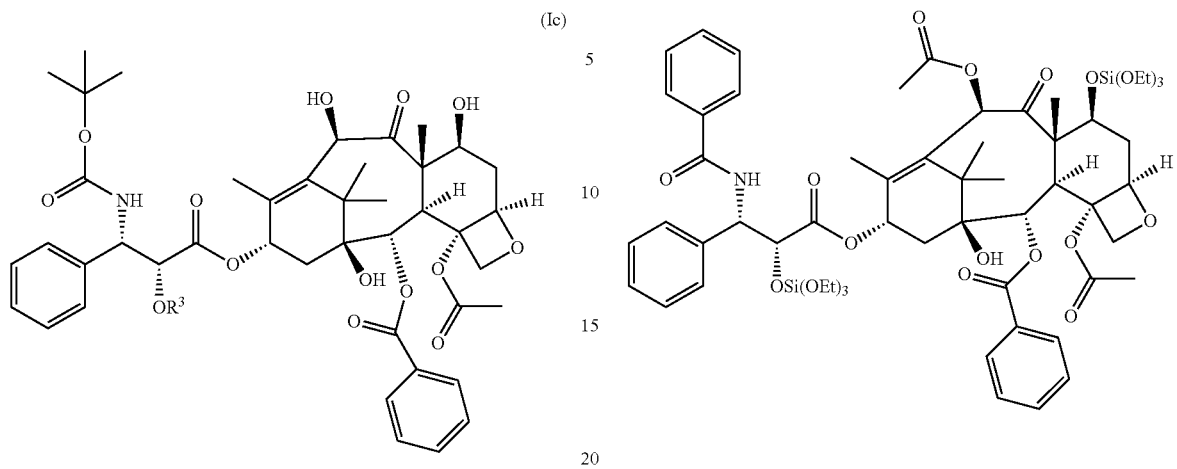
(Ic)
wherein R³ is a group of formula (I), or a salt thereof.
In one embodiment of the invention provides a compound of formula (Id):
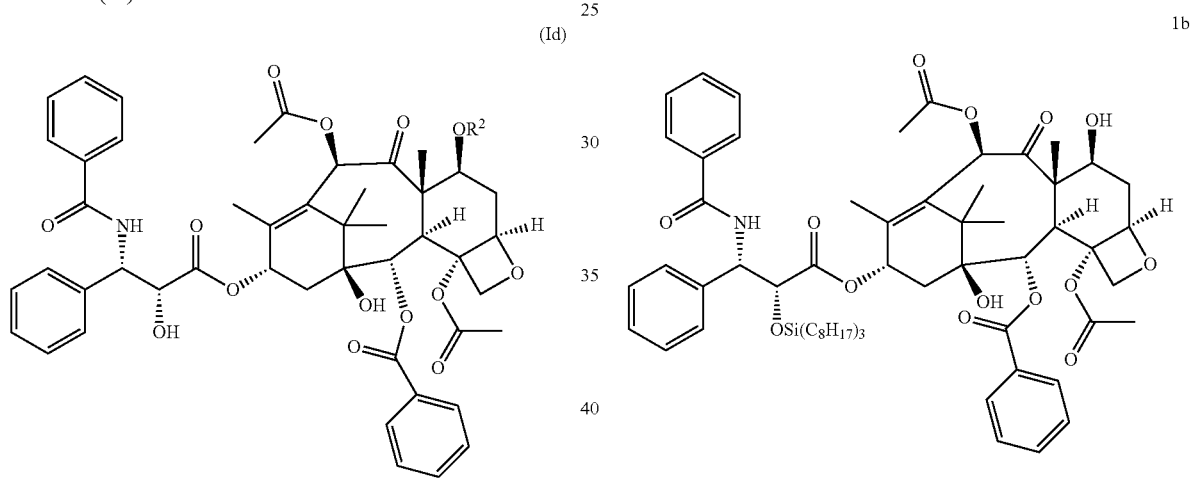
(Id)
wherein R² is a group of formula (I), or a salt thereof.
In one embodiment of the invention the compound of formula (I) is selected from:
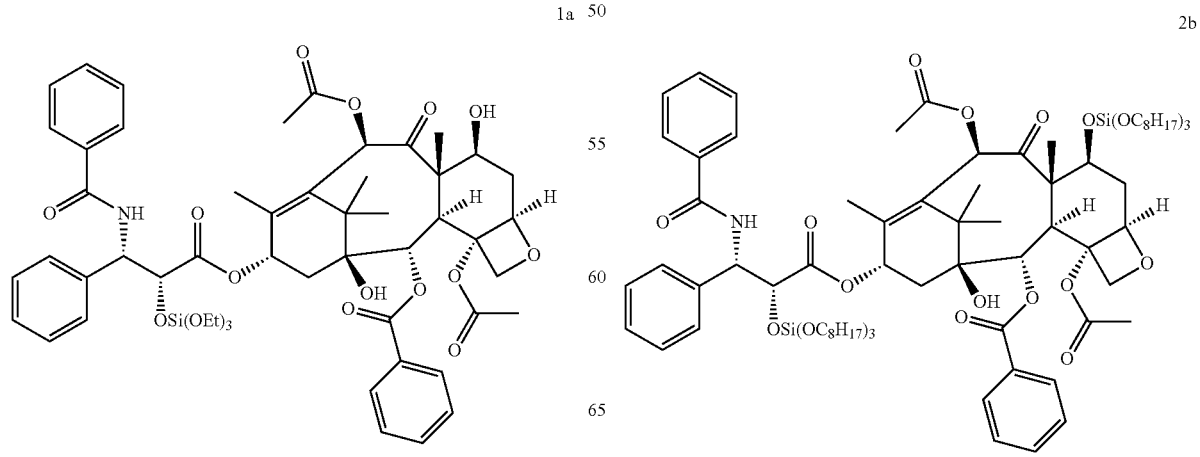
1a
2a
1b
2b

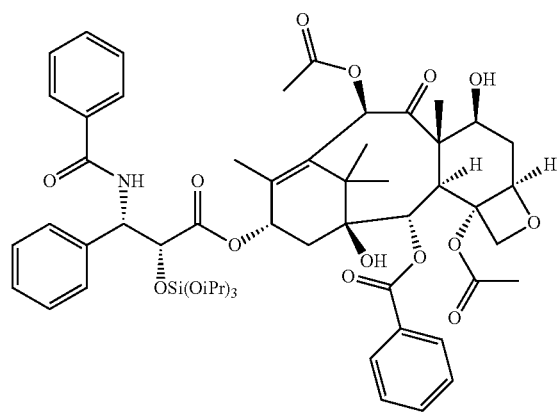
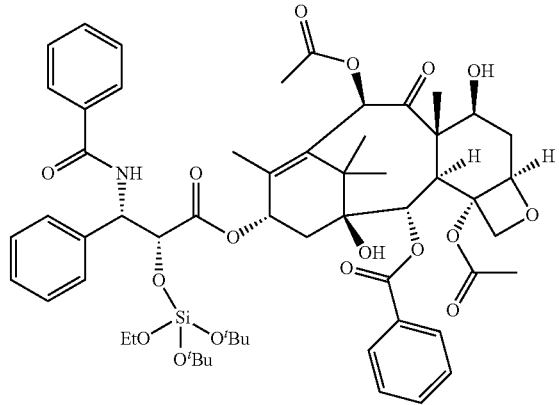
and salts thereof.

In one embodiment of the invention provides a compound selected from:
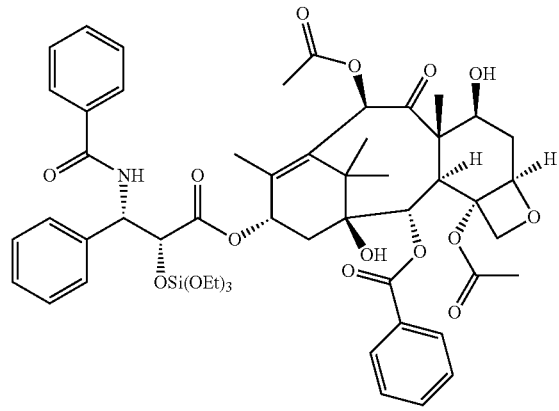
1a
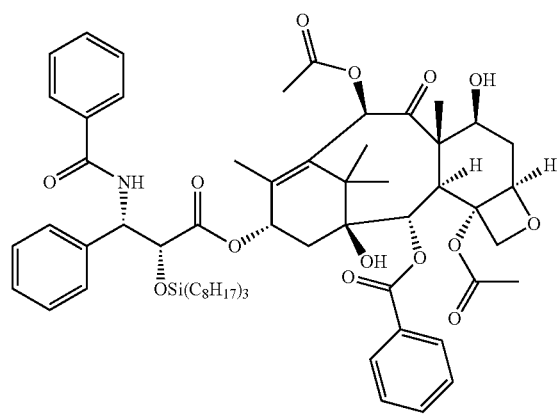
1b
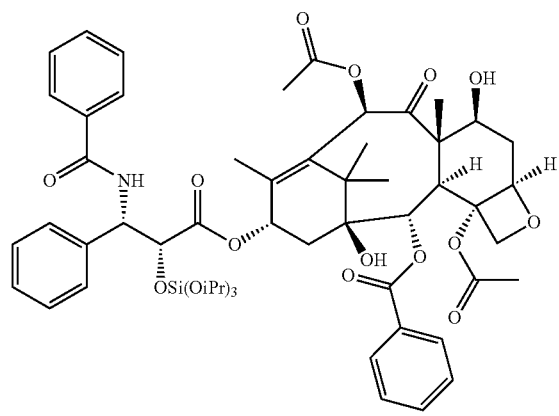
1c
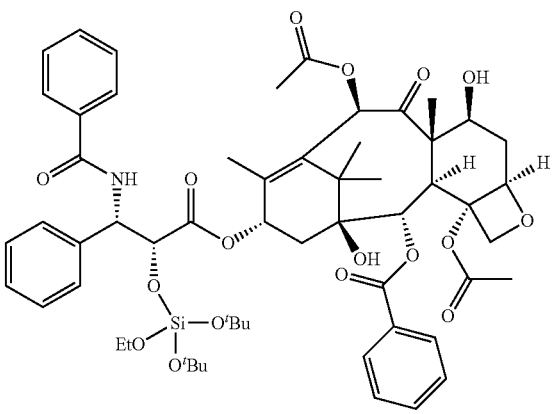
1d
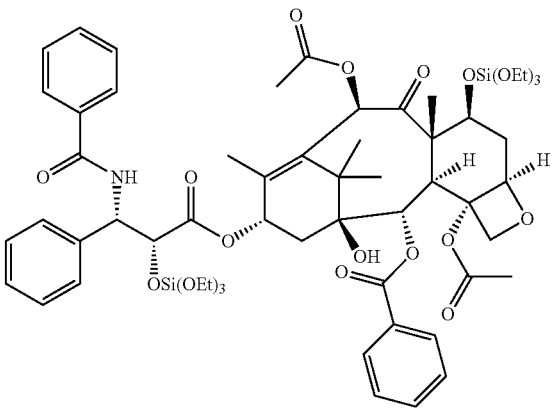
2a
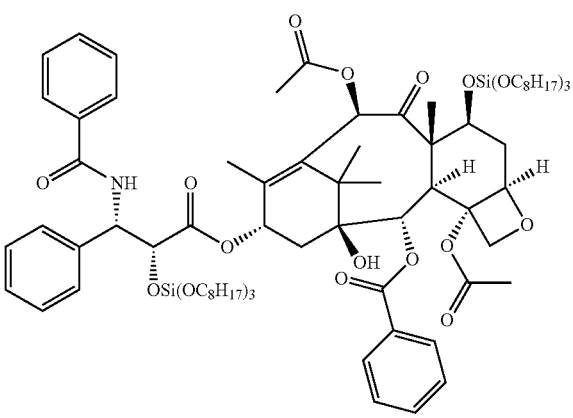
2b 3a

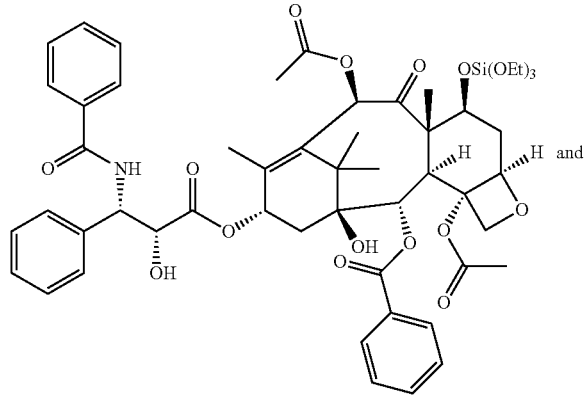

3b

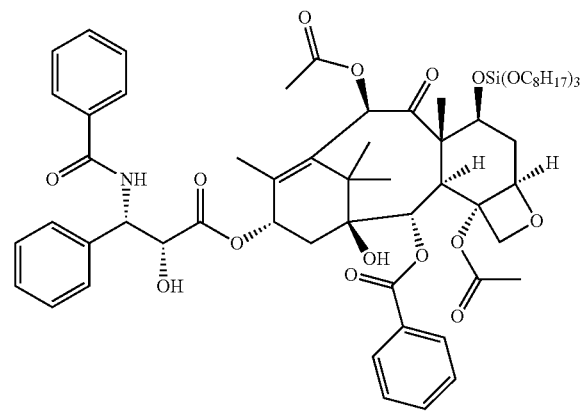

and salts thereof.

Processes for preparing compounds of the invention are provided as further embodiments of the invention and are illustrated by the following procedures in which the meanings of the generic radicals are as given above unless otherwise qualified.

In cases where compounds are sufficiently basic or acidic, a salt of a compound of the invention can be useful as an intermediate for isolating or purifying a compound of the invention. Additionally, administration of a compound of the invention as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patients diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Nanoparticle Preparation

Nanoparticles of the invention can be prepared using well known methods, including multijet vortex mixing as described by Liu, Y., Cheng, C. Y., Liu, Y., Prud'homme, R. K., Fox, R. O., *Chem Eng Sci.* 2008, 63, 2829-2842; impinging jet mixing as described by U.S. PPA 2004/0091546A1, Johnson, B. K. and Prud'homme, R. K., *AIChE Journal,* 2003, 49, 9, 2264-2282 and Johnson, B. K. and Prud'homme, R. K., *Aust. J. Chem,* 2003, 56, 1021-1024; and emulsion methods as described by Patil Y B, Toti U S, Khdair A, Ma L, Panyam J., Single-step surface functionalization of polymeric nanoparticles for targeted drug delivery. Biomaterials. 2009 February; 30(5):859-66.

Silicate prodrugs can be loaded at high levels (>50 wt % paclitaxel) into particles that will be stable in intravenous circulation, will accumulate in tumors, and will release paclitaxel to effectively inhibit tumor growth. Using an impingement jet mixer, an attempt was made to encapsulate unmodified paclitaxel. A solution of THF containing equal masses of PEG-b-PLGA and paclitaxel was impinged under turbulent mixing against an equal volume of water and the effluent immediately (<1 sec) diluted into water. The solvent ratio of the resulting NP suspension was 95:5 $H_2O$:THF. Dynamic light scattering (DLS) measurements of this suspension were recorded. Initially, the diameters of these loaded NPs were ca. 100 nm, but they proved to be unstable. Rapid Ostwald ripening ensued within 90 minutes; that is, paclitaxel left the NP core and reprecipitated, this time as large (>>1 μm) crystals.

In contrast, the particles made from equal masses of the same BCP and the paclitaxel bis-triethyl silicate compound 2a were also formed with small mass average diameters ($d_m$=150 nm), but were stable in suspension for at least 4 days (even in the presence of 1% NaCl). It appears that the presence of the two triethyl silicate groups in 2a sufficiently increases the hydrophobicity of paclitaxel to slow Ostwald ripening.

In one embodiment of the invention the paclitaxel silicate prodrug will be sufficiently hydrophobic to be efficiently co-precipitated into a NP during FNP in order to achieve high loading levels of the taxane prodrug. The ideal prodrug will be identified by its manageable stability during preparation, purification, encapsulation, and formulation storage lifetime, yet its rate of hydrolysis at a tumor site will be pharmacologically effective. Since the prodrug solubility in water will be quite low, premature release of the prodrug from the NPs into the blood prior to localization of the loaded NPs at tumor sites can be expected to be minimal. The prodrug hydrophobicity can be modified using an array of safe aliphatic alcohols of increasing aliphatic character (e.g, ethanol, decanol, geraniol, and phytol) to prepare the requisite $SiCl(OR)_3$ reagents for synthesis of prodrug candidates.

The nanoparticles of the invention are particularly advantageous as potential therapeutic agents because i) they can be prepared in a size range (50-200 nm) that is attractive from the perspective of enhanced permeation and retention (EPR) into and by solid tumors and ii) they can be formulated to comprise at least 50 wt % of the prodrug.

Synthesis of Block Copolymers.

It was determined that PEG-b-PLGA BCPs with narrow polydispersity (PDI≤1.1) could be prepared by DBU-catalyzed (1,8-diazabicyclo[5.4.0]undec-7-ene) ring-opening co-polymerization of lactide and glycolide using Me-PEG-OH as the initiator (Lohmeijer, B. G. G., et al., Guanidine and Amidine Organocatalysts for Ring-Opening Polymerization of Cyclic Esters. *Macromolecules* 2006, 39, 8574-8583). The key to success here was controlled infusion of the more reactive glycolide monomer throughout the polymerization reaction. Notably, this approach allows i) the avoidance of toxic tin catalysts and ii) reliable preparation of a homologous series of related and well-defined BCPs for use in NP optimization studies. To understand and optimize their impact on the properties of silicate loaded NPs, a series of BCPs that vary in block size, block ratio, and glycolide:lactide ratio (within the random polyester hydrophobic block) can be made and assessed. Specifically, PEG-b-PLGAs of the following sizes: 5K/5K, 5K/10K, 5K/15K and 10K/5K, 10K/ 10K, 10K/20K can be prepared. Nanoparticles can be loaded and then assessed for controllability of NP size; efficiency of capturing silicate prodrug; stability upon freeze drying, resuspension in buffer, and storage; and hydrolysis/release behavior. For the best performing BCP, the effect of changing the glycolide:lactide composition within the PLGA from 50:50 (e.g. to 80:20) can be assessed.

A variety of block co-polymers can be used to prepare the formulations and nanoparticles of the invention. For example, any biocompatible block copolymer with a varying number of blocks can, in principle, be used. Typically the hydrophilic block will be a polyether and the hydrophobic block will be a polyester, polyamino acid, polyamine, polyimine, polyamide, polycarbonate, or polycarbamate, etc. Other hydrophobic blocks may include polyethylene, polystyrene, etc. Suitable block co-polymers can be prepared using any suitable method, including the methods described herein as well as the methods described by Afsaneh LaVasanifar, et al., *J. Pharmaceutical Sciences,* 2003, 92, no. 7; and Omathanu Pillai and Ramesh Panchagnula, *Current Opinion in Chemical Biology,* 2001, 5, issue 4, pages 447-451.

Therapeutic Agents.

In principle, any drug with a derivatizable hydroxyl group can be modified with an electrophilic silylating agent, such as a trialkoxychlorosilane, resulting in a silicate ester prodrug. Hydrolytic cleavage catalyzed by a weak acid returns the parent drug. It should be noted that a number of studies imply that orthosilicic acid [$Si(OH)_4$], the byproduct of this prodrug cleavage, should not impose a significant health risk (see Gitelman H J, et al., *Kidney Int,* 1992, 42:957-959; and Marco-Franco J E, et al., 1991, *Clin Nephrol,* 35:52-58).

In one embodiment of the invention the therapeutic agent is an anti-cancer agent that bears one or more hydroxy groups. In another embodiment of the invention the therapeutic agent is a taxane. (see for example, Katsetos C D, Dráber P, Tubulins as Therapeutic Targets in Cancer: from Bench to Bedside, Curr Pharm Des. 2012 Feb. 28. [Epub ahead of print]; Singh S, Dash A K., Paclitaxel in cancer treatment: perspectives and prospects of its delivery challenges, Crit Rev Ther Drug Carrier Syst. 2009; 26(4):333-72; and Natural *Taxanes*: Developments Since 1828. Wang, Yu-Fang; Shi, Qing-Wen; Dong, Mei; Kiyota, Hiromasa; Gu, Yu-Cheng; Cong, Bin Chemical Reviews (Washington, D.C., United States) (2011), 111(12), 7652-7709). In another embodiment of the invention the therapeutic agent is paclitaxel or docetaxel.

Figure 4:
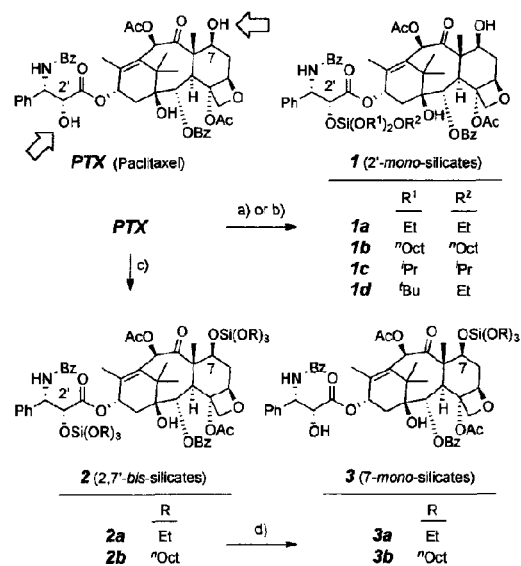
FIG. 4 Illustrates the preparation of representative compounds of the invention.

Representative compounds of the invention were prepared from PTX as outlined in FIG. 4.

Controlled Release Rates

The silicate prodrugs of the invention can be designed to have varying hydrophobicity and, independently, different rates of hydrolysis. Accordingly, different silicate prodrugs of a single drug (e.g. a taxane) can be designed to provide different rates of hydrolysis. By combining or administering two or more silicate prodrugs having different rates of hydrolysis it is possible to deliver a drug (e.g. a taxane) with a specifically designed release profile. For example, it is possible to administer compounds of the invention so that a controlled level of the drug (e.g. the taxane) is delivered over an extended period (e.g. 1-2 weeks) of time.

Accordingly, in one embodiment the invention provides a pharmaceutical composition comprising a) two or more compounds of the invention; and b) a pharmaceutically acceptable carrier. For example, the pharmaceutical composition can comprise a first compound of the invention that comprises a taxane linked to one group of formula (I), and a second compound of the invention that comprises a taxane linked to two or more groups of formula (I). As another example, the pharmaceutical composition of the invention can comprise a first compound of the invention that comprises a taxane linked to one or more groups of formula (I) wherein R has a first value, and a second compound of the invention that comprises a taxane linked to one or more groups of formula (I) wherein R has a second (different) value. It will be apparent that other pharmaceutical compositions having variable release profiles can be prepared by altering the number of groups of formula (I) and/or by altering the value for R in the compounds of the invention.

In another embodiment the invention provides a method to treat cancer in an animal comprising administering to the animal two or more different compounds of the invention. In another embodiment the invention provides a method to treat cancer in an animal comprising administering to the animal a formulation of the invention that comprises two or more different compounds of the invention. In another embodiment the invention provides a method to treat cancer in an animal, comprising administering to the animal a nano-particle of the invention that comprises two or more different compounds of the invention. In another embodiment the invention provides a method to treat cancer in an animal, comprising administering to the animal a first nano-particle of the invention that comprises one compound of the invention and a second nano-particle of the invention that comprises a different compound of the invention. For example, the compound of the invention in the first nano-particle and the compound of the invention in the second nano-particle can be selected to provide a selected release profile of the drug (e.g. the taxane) over a selected period of time.

In another embodiment the invention provides a nano-particle comprising two or more different compounds of the invention. For example, the compounds of the invention can be selected to provide a selected release profile of the drug (e.g. the taxane) over a selected period of time upon administration of the nano-particle.

Combination Therapy

The silicate prodrugs of the invention can be administered or used in combination with one or more additional therapeutic agents. The additional agent(s) can be administered separately or sequentially with the silicate prodrugs of the invention or they can be co-formulated with one or more silicate prodrugs of the invention.

Suitable additional therapeutic agents that can be administered with or co-formulated with the silicate prodrugs of the invention include anti-cancer agents such as, for example, all-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Mechlorethamine, Mercaptopurine, Methotrexate, Mitoxantrone, Oxaliplatin, PaclitaxelPemetrexed, Teniposide, Tioguanine, Valrubicin, Vinblastine, Vincristine, Vindesine, Vinorelbine, and selective and non-selective tyrosine kinase inhibitors (e.g. lapatinib, dasatanib, vemurafinib, imatinib, gefitinib, erlotinib, and sunitinib, etc.). Other additional therapeutic agents that can be administered with or co-formulated with the silicate prodrugs of the invention include P-gp inhibitors (verapamil, cyclosporine, tariquidar, elacridar, etc) and CYP3A4 inhibitors (ritonavir, indinavir, nelfinavir, saquinavir, clarithromycin, bergamottin, cimetidine, voriconazole, fluoxetine/norfluoxetine, piperine, and silibinin, quercetin, etc).

Accordingly, in one embodiment the invention provides a pharmaceutical composition comprising a) a compound of the invention; b) one or more additional therapeutic agents; and c) a pharmaceutically acceptable carrier.

In another embodiment the invention provides a method to treat cancer in an animal comprising administering to the animal a compound of the invention, or a formulation of the invention, or a nano-particle of the invention in combination with one or more additional therapeutic agents.

In another embodiment the invention provides a nano-particle comprising a compound of the invention and one or more additional therapeutic agents. For example, the additional therapeutic agent(s) can be coated on a nano-particle comprising a compound of the invention or the additional therapeutic agent(s) can be incorporated into a nano-particle of the invention.

Targeted Therapy

The nano-particles of the invention can also incorporate one or more targeting groups that will facilitate delivery of the nano-particles to specific sites (e.g. tumors) in the body. For example, in one embodiment of the invention, the nano-particles of the invention can further comprise one or more targeting moieties that target a site on a tumor cell, for example, an EGFR that is overexpressed on many tumor cells.

Targeting moieties that can be incorporated into the nano-particles of the invention include: folic acid, biotin, a Cys-Arg-Glu-Lys-Ala (CREKA) peptide, mannose 6-phosphate, transferrin, a peptide targeting trasferrin receptor, an epidermal growth factor receptor (EGFR) targeting peptide, an scFv or antibody, a CD133 targeting scFv or antibody, and peptides targeting the integrin receptors.

In one embodiment of the invention, the targeting moiety can also possess its own therapeutic activity. Such targeting moieties can include: TRAIL, Cetuximab, Trastuzumab, Bevacizumab, Rituximab, Ibritumomab, Tositumomab, Alemtuzumab, and Epratuzumab.

The targeting moieties can be incorporated into the nano-particles in any suitable manner. For example, the targeting moieties can be associated with the nano-particles in a non-covalent manner, or the targeting moieties can be covalently bonded to the nano-particles either directly or through a suitable linker. In one embodiment of the invention, the targeting moiety can be linked to a polymer component (e.g. a PEG-b-PLGA block co-polymer) of a nano-particle.

Scheme 1 illustrates the preparation of a PEG-b-PLGA block co-polymer that is linked to a targeting moiety (an EGFRP). This PEG-b-PLGA block co-polymer can be incorporated into nano-particles of the invention. The non-functionalized copolymer 1, can be converted to the maleimide (MAL) functional BCP 2 (for use in surface ligation), which can be attached to a targeting moiety (e.g. EGFRP) to provide and the final BCP 3, which carries a covalently bound EGFR targeting moiety.

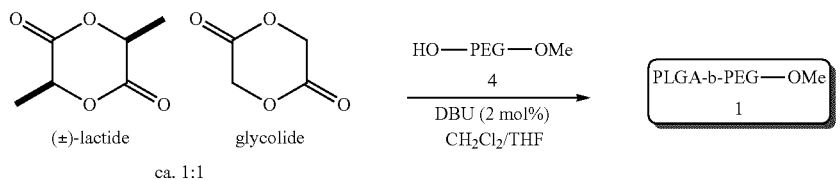

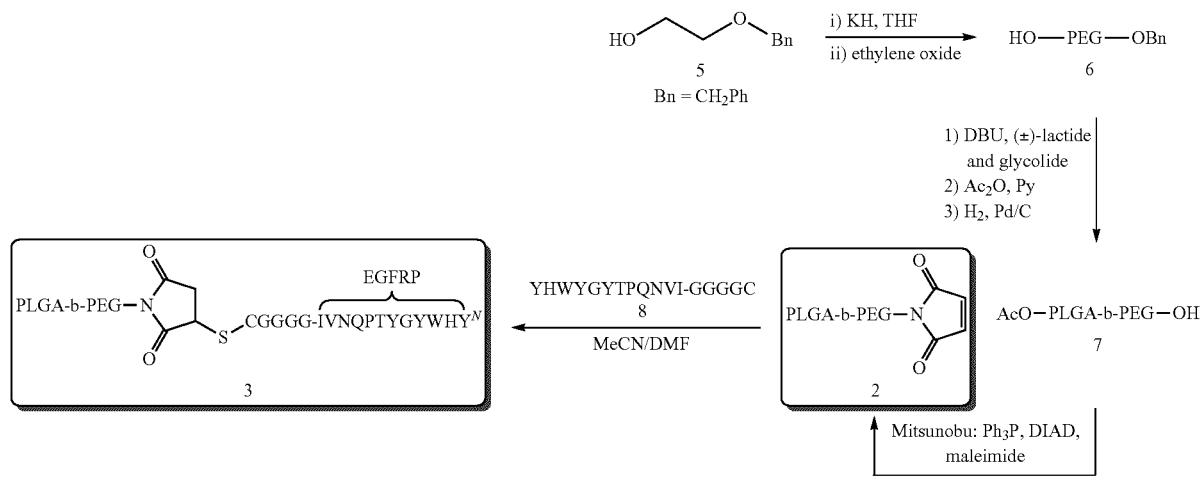

Scheme 2 illustrates the preparation of nano-particles of the invention using the polymer components described in Scheme 1 above. The surface reactive particles $NP^{MAL}$, which are obtained from FNP of a prodrug and the BCPs 1 and 2, can be used as key intermediates. In situ surface conjugation to the reactive MALs in $NP^{MAL}$ by reaction with the cysteine-containing peptide 8 can be used to introduce an EGFRP targeting moiety. For this (as well as the synthesis of $NP^{Cmab}$) any remaining MAL groups can be capped by incubation with excess Cys. Note that the surface density of the targeting moiety present in the final nano-particle can be readily controlled by adjusting the ratio of either 2 or 3 vs. 1 as well as by the amount of 8 used in the derivatization of $NP^{MAL}$.

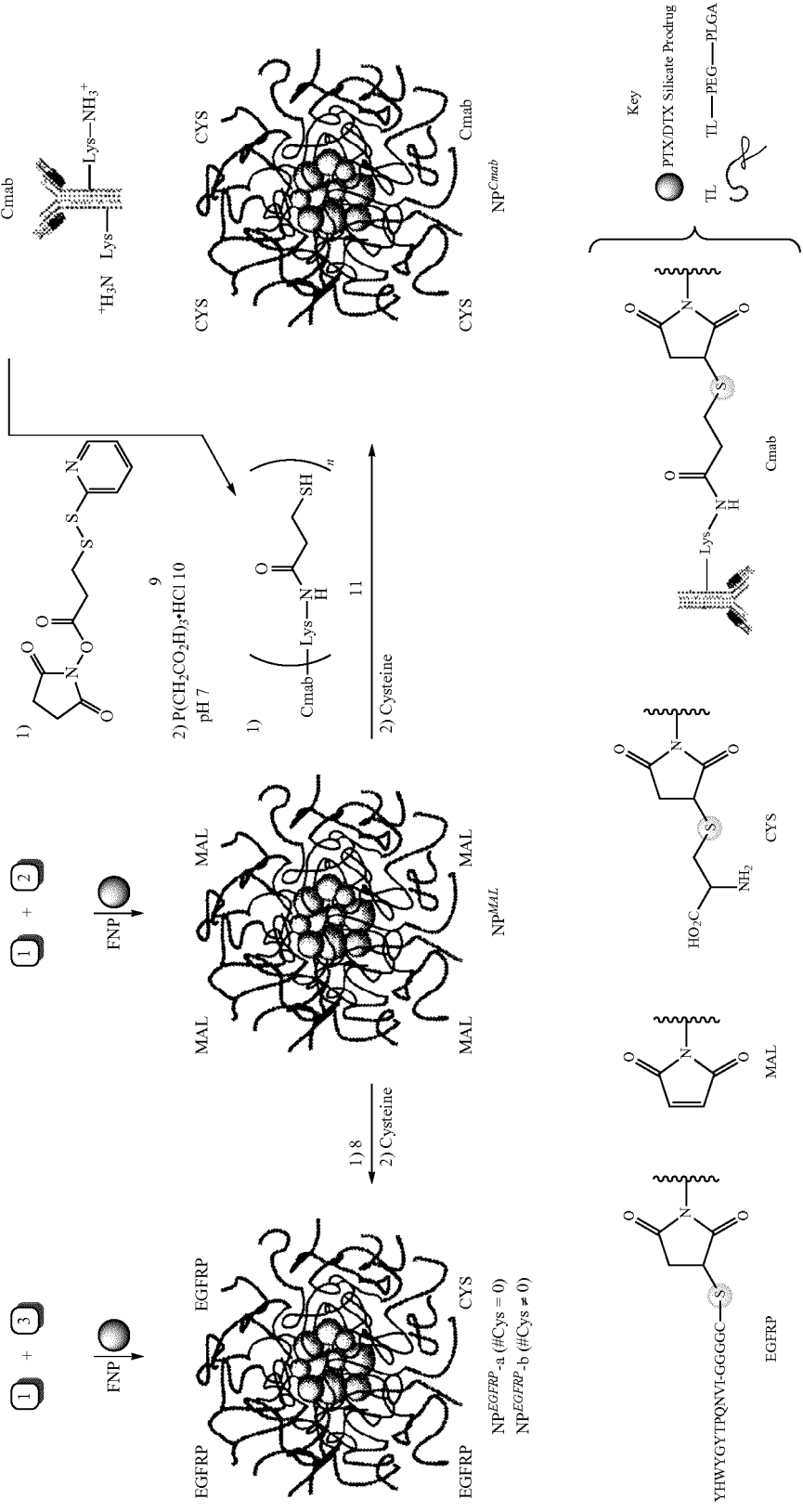
Scheme 2. Complementary strategies for incorporating Targeting Moieties selective for EGFR-positive tumor cells on the surface of prodrug-loaded NPs.

To prepare the Cmab—carrying particles—i.e., $NP^{Cmab}$-Cmab the 250 kDa antibody will first be thiolated by N-acylation of a few surface lysines with the disulfide 9, followed by reduction to the free thiol 11 with the water-soluble phosphine 10. Again, ligation through covalent bond formation between 11 and the MALs in the preformed $NP^{MAL}$ will provide the prodrug-loaded $NP^{Cmab}$.

The Mal-substituted polymers and nano-particles ($NP^{MAL}$) described in Schemes 1 and 2 are useful intermediates for preparing the nano-particles of the invention and they represent embodiments of the invention.

Accordingly, in one embodiment the invention provides a nano-particle comprising a compound of the invention and one or more targeting moieties.

The in vivo activity of a compound or a formulation of the invention can be evaluated using the following model.

In Vivo Activity

A mouse xenograft tumor model, employing 6-8 week old ovariectomized female NCRNU-M mice (Taconic Farms), can be used. MCF-7 cells ($5 \times 10^6$) can be used to induce tumors. Tumor growth will be facilitated by estrogen pellet implantation. A total of 324 animals are required for the studies [126 for study 1 (biodistribution study), 36 for study 2 (tumor growth inhibition study); two repeats].

Pellet Implantation:

Ovariectomized mice (Taconic Farms) can be used in order to avoid complications from ovarian response to elevated estrogen levels. Following 1 week acclimatization, animals can be implanted with estradiol pellets. To implant pellets, mice can be anesthetized with ketamine (80 mg/kg) and xylazine (7 mg/kg) intraperitoneally using a 26 gauge needle. Following swabbing of the site with betadine (twice with circular motion from center to periphery), the estradiol pellet (ca. 2 mm in diameter) can be implanted under the skin with a sterile trocar, and the implantation site can be closed with tissue adhesive (Liquivet Rapid). Animals can be placed in cages on paper towels until recovery. During recovery the cages can be placed on a heating pad at low setting. Animals can be observed until mobility is recovered. No additional analgesics can be administered. All procedures can be performed under aseptic conditions.

Tumors can be induced by subcutaneous injection of $5 \times 10^6$ MCF-7 tumor cells suspended in 0.05 mL of Hank's phosphate buffered saline on the right flank. The subcutaneous injection can be administered using a 26-gauge needle. Tumor induction can be done two-three days following pellet implantation.

Tumor volume can be monitored on a regular basis using calipers. Length (L) and width (W) of the tumor can be measured and its volume calculated using the equation: $(L \times 2W)/2$. Tumor volume and body weight can be measured every alternate day during the first month and twice a week in the 2nd and 3rd month after treatment administration.

Animals that develop 100-200 mm$^3$ size tumors can be randomized into different treatment groups (see Specific Aim 3 methods). Tumor-bearing mice can be treated with single intravenous injection of different treatments in 200 µL of Hank's balanced salt solution using a 27-gauge needle. For biodistribution studies, animals can be treated and then euthanized (1 h, 6 h, 12 h, 24 h, 3 days, 1 week, and 2 weeks) for the collection of blood and other tissues. For tumor growth inhibition studies, animals can be observed for tumor growth and mortality over a 30-day period. Animals can also be observed for body weight.

Animals that demonstrate weight loss of more than 20% of the initial weight and/or tumor weight equal to or more than 10% of the body weight can be removed from the study and euthanized.

The invention will now be illustrated by the following non-limiting Examples.

EXAMPLES

General

Paclitaxel was obtained from Phytogen Life Sciences. Triethylamine and pyridine were purchased from Sigma Aldrich and purified by distillation over $CaH_2$. Triethoxychlorosilane was purchased from Gelest. Silicon tetrachloride was purchased from Sigma Aldrich and transferred to a Schlenk flask under nitrogen and used to synthesize the tri-n-octyloxychlorosilane, tri-i-propoxychlorosilane, and di-t-butoxydichlorosilane [using n-octanol, i-propanol, and t-butanol (all purchased from Sigma Aldrich and dried over activated 3 Å molecular sieves overnight), respectively]. Tetrahydrofuran was purchased from Fisher Scientific and dried by being passed through an actived alumina column. Ethanol (200 proof) was purchased from Decon Labs, Inc and further dried by storing over activated 3 Å molecular sieves overnight. Ethyl acetate (ACS grade) was purchased Macron Chemicals and used as received. Hexanes (ACS grade) were purchased from Fisher Scientific and used as received. The $d_6$-acetone and d-chloroform was purchased from Cambridge Isotope Laboratories, Inc. and dried over activated 3 Å molecular sieves overnight. $D_2O$ was purchased from Cambridge Isotope Laboratories, Inc. and used as received.

Abraxane (Abraxis Biosciences, Los Angeles, Calif., USA) was obtained from the Boynton health services pharmacy, University of Minnesota Twin Cities. Matrigel and D-Luciferin dipotassium salt were obtained from BD Pharmingen (San Diego, Calif., USA). The PEG-b-PLGA block copolymer was synthesized as previously reported (see Qian H, et al., *Macromolecules*, 2011, 44:7132-7140).

Medium Pressure Liquid Chromatography (MPLC) purifications were performed using columns dry packed with ca. 25-35 µm silica gel. The MPLC apparatus was pressurized with a Waters Chromatography Pump. Compound detection was performed by using a Gilson Model 111B UV Absorbance detector at 254 nm and a Waters Differential Refractometer in sequence. All thin layer chromatography (TLC) data was collected on glass-backed plates coated with F-254 indicator obtained from SiliCycle. Visualization was completed via UV-light and/or staining with phosphomolybdic acid (PMA). $^1H$ NMR spectra were taken on a Varian VI-500 (500 MHz $^1H$). All $^1H$ characterization spectra were taken in $CDCl_3$ and chemical shifts (δ) are referenced to tetramethylsilane at δ=0.00. All $^{13}C$ NMR characterization spectra were taken in $CDCl_3$ on either a Bruker AV-500 (125 MHz $^{13}C$) or a Varian VI-300 (75 MHz $^{13}C$) and referenced to $CHCl_3$ at δ=77.23. The following abbreviations are used to describe the NMR signals: s (singlet), d (doublet), t (triplet), q (quartet), sept (septet), m (multiplet), br (broad), and app (apparent). Coupling constants (J) are reported in Hz. Infrared spectra were recorded using a Midac Corporation Prospect 4000 FT-IR. All samples were collected in attenuated total reflectance mode as thin films on a germanium window. Melting point data were collected on a Köfler hot stage and are uncorrected. High resolution mass spectra were collected on a Bruker BioTOF II (ESI-TOF) instrument using poly(ethylene glycol) (PEG) or poly(propylene glycol) (PPG) as an internal standard.

Example 1

Preparation of 2',7-Di-O-(triethyl orthosilyl)paclitaxel (2a)

Paclitaxel (58.0 mg, 0.0679 mmol, 1.0 equiv) was dissolved in dry THF (1.0 mL) in an oven-dried culture tube fitted with a Teflon-lined cap and a stir bar. Pyridine (25 μL, 0.309 mmol, 4.5 equiv) was added by Wiretrol®. Chlorotriethoxysilane (50 μL, 0.255 mmol, 3.8 equiv) was added, and a white precipitate was immediately observed. The suspension was allowed to stir for 2 hours at room temperature and then diluted with hexanes:EtOAc (1:1). The slurry was filtered through a short plug of Celite® to remove the pyridinium salt, and the filtrate concentrated under reduced pressure. The residue was purified by MPLC ($SiO_2$, 2:1 hexanes:EtOAc) to yield 2a as a white crystalline solid (68.0 mg, 0.058 mmol, 85%). If necessary, residual EtOAc was removed by storage under high vacuum for ≥24 h. $^1$H NMR (500 MHz, $CDCl_3$): δ 8.12 (dd, J=8.5, 1.5 Hz, 2H, $C2O_2C$-o-Ph), 7.78 (dd, J=8.5, 1.5 Hz, 2H, C3'NHCO-o-Ph), 7.62 (tt, J=7.5, 1.0 Hz, 1H, $C2O_2C$-p-Ph, 1H), 7.54-7.46 (m, 3H, $C2O_2C$-m-Ph and C3'NHCO-p-Ph), 7.44-7.36 (m, 6H, C3'-o-Ph, C3'-m-Ph and C3'NHCO-m-Ph), 7.29 (tt, J=7.0, 1.5 Hz, 1H, C3'-p-Ph), 7.20 (d, J=8.5 Hz, 1H, C3'NH), 6.58 (s, 1H, H10), 6.18 (br dd, J=9, 9 Hz, 1H, H13), 5.72 (dd, J=8.5, 3.0 Hz, 1H, H3'), 5.71 (d, J=6.5 Hz, 1H, H2), 4.98 (d, J=3.0 Hz, 1H, 2'H), 4.96 (dd, J=10.0, 2.0 Hz, 1H, H5), 4.62 (dd, J=10.5, 6.7 Hz, 1H, H7), 4.31 (d, J=8.5 Hz, 1H, H20α), 4.20 (d, J=8.5 Hz, 1H, H20β), 3.85 (d, J=7.0 Hz, 1H, H3), 3.76 [q, J=7.0 Hz, 6H, C7OSi($OCH_2CH_3$)$_3$], 3.71 [q, J=7.0 Hz, 6H, C2'OSi($OCH_2CH_3$)$_3$], 2.66 (ddd, J=14.5, 9.5, 6.5 Hz, 1H, H6α), 2.45 (s, 3H, C4OAc), 2.33 (dd, J=15.4, 9.4 Hz, 1H, H14α), 2.15 (s, 3H, C10OAc), 2.08 (d, J=1.5 Hz, 3H, $C18H_3$), 2.07 (dd, J=15.1, 9.0 Hz, 1H, H14β), 1.96 (ddd, J=14.5, 10.8, 2.2 Hz, 1H, H6β), 1.73 (s, 3H, $C19H_3$), 1.65 (br s, 1H, C1OH), 1.23 (s, 3H, $C17H_3$), 1.19 [t, J=7.0 Hz, 9H, C7OSi($OCH_2CH_3$)$_3$], 1.17 (s, 3H, $C16H_3$), and 1.15 [t, J=7.0 Hz, 9H, C2'OSi($OCH_2CH_3$)$_3$]. $^{13}$C NMR (75 MHz, $CDCl_3$): 202.6, 171.0, 169.8, 169.0, 167.3, 167.2, 141.0, 138.2, 134.3, 133.9, 133.3, 132.0, 130.4, 129.4, 128.9, 128.8, 128.7, 128.1, 127.3, 126.8, 84.5, 81.2, 78.9, 76.7, 75.9, 75.02, 74.99, 72.1, 71.6, 59.7, 59.5, 58.3, 55.5, 46.9, 43.4, 36.5, 35.5, 26.7, 23.0, 21.4, 21.0, 18.0 (×2), 14.2, and 10.4. HRMS (ESI) Calcd for $C_{59}H_{79}NNaO_{20}Si_2$ [M+Na]$^+$1200.4626, found 1200.4631. IR (thin film) 3500 (br), 2976, 2928, 2896, 1744, 1725, 1644, 1603, 1580, 1541, 1486, 1451, 1370, 1314, 1268, 1238, 1169, 1098, 1080, 1027, 969, 891, 842, 795, and 708 cm$^{-1}$. mp=121-123° C. TLC $R_f$ (2:1 Hexanes:EtOAc)=0.4.

Example 2

Preparation of 2'-O-(triethyl orthosilyl)paclitaxel (1a)

Paclitaxel (55.3 mg, 0.0648 mmol, 1.0 equiv) was dissolved in dry THF (1.0 mL) in an oven-dried culture tube fitted with a Teflon-lined cap and magnetic stir bar. Triethylamine (20 μL, 0.130 mmol, 2.0 equiv) was added by Wiretrol®. Chlorotriethoxysilane (25 μL, 0.0127 mmol, 2.0 equiv) was then added, and a white precipitate was immediately observed. The culture tube was sealed and the suspension was allowed to stir for 1 hour at room temperature. The reaction slurry was diluted with a mixture of hexanes:EtOAc (1:1) and filtered through a short plug of Celite® to remove the triethylammonium salt. The filtrate was concentrated under reduced pressure, and the residue redissolved in a mixture of hexanes:EtOAc (1:1). Chromatography ($SiO_2$, 1:1 hexanes:EtOAc) via MPLC yielded the title compound as a white, crystalline solid (59.6 mg, 0.0587 mmol, 90.6%). If necessary, residual EtOAc was removed by storage under high vacuum for ≥24 h. $^1$H NMR (500 MHz, $CDCl_3$): δ 8.12 (dd, J=8.5, 1.4 Hz, 2H, $C2O_2C$-o-Ph), 7.78 (dd, J=8.5, 1.3 Hz, 2H, C3'NHCO-o-Ph), 7.62 (tt, J=7.5, 1.2 Hz, 1H, $C2O_2C$-p-Ph, 1H), 7.56-7.46 (m, 3H, $C2O_2C$-m-Ph and C3'NHCO-p-Ph), 7.43-7.36 (m, 6H, C3'-o-Ph, C3'-m-Ph and C3'NHCO-m-Ph), 7.29 (tt, J=6.5, 2.2 Hz, 1H, C3'-p-Ph), 7.19 (d, J=8.6 Hz, 1H, C3'NH), 6.28 (s, 1H, H10), 6.24 (br dd, J=9, 9 Hz, 1H, H13), 5.72 (dd, J=8.5, 3.2 Hz, 1H, H3'), 5.68 (d, J=7.1 Hz, 1H, H2), 4.97 (dd, J=9.4, 2.0 Hz, 1H, H5), 4.96 (d, J=3.3 Hz, 1H, H2'), 4.43 (ddd, J=10.9, 6.4, 4.5 Hz, 1H, H7), 4.32 (d, J=8.5 Hz, 1H, H20α), 4.20 (d, J=8.5 Hz, 1H, H20β), 3.80 (d, J=7.2 Hz, 1H, H3), 3.71 [q, J=7.0 Hz, 6H, C2'OSi($OCH_2CH_3$)$_3$], 2.56 (ddd, J=14.7, 9.6, 6.5 Hz, 1H, H6α), 2.45 (s, 3H, C4OAc), 2.44 (br s, 1H, C7OH), 2.32 (dd, J=15.4, 9.4, Hz, 1H, H14α), 2.24 (s, 3H, C10OAc), 2.08 (dd, J=15.2, 8.8 Hz, 1H, H14β), 1.90 (d, J=1.2 Hz, 3H, $C18H_3$), 1.89 (ddd, J=14.5, 11.0, 2.4 Hz, 1H, HO), 1.68 (s, 3H, $C19H_3$), 1.64 (br s, 1H, C1OH), 1.24 (s, 3H, $C17H_3$), 1.15 [t, J=7.0 Hz, 9H, C2'OSi($OCH_2CH_3$)$_3$], and 1.13 (s, 3H, $C16H_3$). $^{13}$C NMR (75 MHz, $CDCl_3$): δ 204.0, 171.6, 171.0, 170.1, 167.3, 167.2, 143.0, 138.2, 134.2, 133.9, 132.9, 132.0, 130.4, 129.3, 128.9 (×2), 128.8, 128.2, 127.3, 126.8, 84.6, 81.2, 79.3, 76.7, 75.8, 75.3, 75.1, 72.3, 71.5, 59.7, 58.7, 55.6, 45.7, 43.4, 35.7, 35.6, 27.0, 23.0, 22.4, 21.1, 18.2, 14.9, and 9.8. HRMS (ESI) Calcd for $C_{53}H_{65}NNaO_{17}Si$ [M+Na]$^+$1038.3914, found 1038.3942. IR (thin film) 3500 (br), 2977, 2898, 1744, 1730, 1636, 1580, 1540, 1487, 1452, 1371, 1314, 1268, 1240, 1170, 1145, 1078, 1025, 978, 908, 854, 797, and 710 cm$^{-1}$. mp=131-134° C. TLC $R_f$ (1:1 Hexanes:EtOAc)=0.45.

Example 3

Preparation of 2-O-(tri-n-octyl orthosilyl)paclitaxel (1b)

Paclitaxel (76.0 mg, 0.0890 mmol, 1.0 equiv) was dissolved in dry THF (1.5 mL) in an oven-dried culture tube fitted with a Teflon-lined cap and magnetic stir bar. Triethylamine (60 μL, 0.430 mmol, 4.8 equiv) was added by Wiretrol®. A 1.67:1 mixture of tri-n-octyloxychlorosilane:tetra-n-octyloxysilane (0.200 mg, 0.257 mmol, 2.9 equiv of tri-n-octyloxychlorosilane) was added and a white precipitate was immediately observed. The culture tube was sealed and the suspension was allowed to stir for 22 h at room temperature. The reaction slurry was diluted with a mixture of hexanes:EtOAc (1:1), the slurry filtered through a short plug of Celite® to remove the triethylammonium salt, the filtrate concentrated under reduced pressure, and the residue redissolved in a mixture of hexanes:EtOAc (2:1). Chromatography ($SiO_2$, 2:1 hexanes:EtOAc) via MPLC yielded the title compound as a white, crystalline solid (91.5 mg, 0.0721 mmol, 81.0%). If necessary, residual EtOAc was removed by storage under high vacuum for ≥24 h. $^1$H NMR (500 MHz, $CDCl_3$): δ 8.13 (dd, J=8.5, 1.5 Hz, 2H, $C2O_2C$-o-Ph), 7.77 (dd, J=8.5, 1.4 Hz, 2H, C3'NHCO-o-Ph), 7.62 (tt, J=7.4, 1.3 Hz, 1H, $C2O_2C$-p-Ph), 7.55-7.46 (m, 3H, $C2O_2C$-m-Ph and C3'NHCO-p-Ph), 7.43-7.35 (m, 6H, C3'-o-Ph, C3'-m-Ph and C3'NHCO-m-Ph), 7.28 (tt, J=6.9, 1.7 Hz, 1H, C3'-p-Ph), 7.19 (d, J=8.6 Hz, 1H, C3'NH), 6.28 (s, 1H, H10), 6.25 (br dd, J=9, 9 Hz, 1H, H13), 5.72 (dd, J=8.6, 3.2 Hz, 1H, H3'), 5.68 (d, J=7.1 Hz, 1H, H2), 4.97 (dd, J=9.8, 2.1 Hz, 1H, H5), 4.96 (d, J=12 Hz, 1H, H2'), 4.44 (ddd, J=10.9, 6.7, 4.2 Hz, 1H, H7), 4.31 (d, J=8.4 Hz, 1H, H20α), 4.20 (d, J=8.3 Hz, 1H, H20β), 3.80 (d, J=7.1 Hz, 1H, H3), 3.61 {t, J=6.8 Hz, 6H, C2'OSi[OCH$_2$(CH$_2$)$_6$CH$_3$]$_3$}, 2.56 (ddd, J=14.8, 9.6, 6.6 Hz, 1H, H6α), 2.47 (d, J=4.1 Hz, 1H, C7OH), 2.44 (s, 3H, C4OAc), 2.32 (dd, J=15.4, 9.4 Hz, 1H, H14α), 2.24 (s, 3H, C10OAc), 2.07 (dd, J=15.4, 8.8 Hz, 1H, H14β), 1.89 (d, J=1.4 Hz, 3H, C18H$_3$), 1.89 (m, 1H, H6β, 1.68 (s, 3H, C19H$_3$), 1.65 (br s, 1H, C1OH), 1.48 [tt, J=6.9, 6.9 Hz, 6H, C2'OSi(OCH$_2$CH$_2$(CH$_2$)$_5$CH$_3$)$_3$], 1.32-1.22 {m, 33H, C2'OSi[OCH$_2$CH$_2$(CH$_2$)$_5$CH$_3$]$_3$ and C17H$_3$}, 1.13 (s, 3H, C16H$_3$), and 0.88 {t, J=6.9 Hz, 9H, C2'OSi[OCH$_2$CH$_2$(CH$_2$)$_5$CH$_3$]$_3$}. $^{13}$C NMR (75 MHz, CDCl$_3$): δ 204.0, 171.5, 170.9, 170.1, 167.2, 167.2, 143.0, 138.3, 134.3, 133.9, 132.9, 132.0, 130.4, 129.3, 128.9 (×2), 128.8, 128.1, 127.3, 126.8, 84.7, 81.2, 79.3, 76.6, 75.8, 75.3, 74.9, 72.4, 71.4, 64.1, 58.7, 55.5, 45.7, 43.4, 35.8, 35.7, 32.4, 32.0, 29.54, 29.52, 27.0, 25.8, 23.0, 22.9, 22.4, 21.1, 14.9, 14.3, and 9.8. HRMS (ESI) Calcd for C$_{71}$H$_{101}$NNaO$_{17}$Si [M+Na]$^+$1290.6731. found 1290.6749. IR (thin film) 2926, 2855, 1730, 1665, 1643, 1602, 1581, 1518, 1484, 1453, 1371, 1312, 1271, 1240, 1174, 1094, 1025, 985, 926, 907, 851, 801, 777, and 711 cm$^{-1}$. mp=60-63° C. TLC R$_f$ (3:1 Hexanes:EtOAc)=0.15.

Example 4

Preparation of 2'-O-(tri-i-propyl orthosilyl)paclitaxel (1c)

Paclitaxel (38.8 mg, 0.0454 mmol, 1.0 equiv) was dissolved in dry THF (1.0 mL) in an oven-dried culture tube fitted with a Teflon-lined cap and magnetic stir bar. Triethylamine (25 μL, 0.179 mmol, 3.9 equiv) was added by Wiretrol®. A 2.9:1 mixture of tri-i-propoxychlorosilane:tetra-i-propoxysilane (0.155 mg, 0.132 mmol, 2.9 equiv of tri-i-propoxychlorosilane) was added. The culture tube was sealed and a white precipitate was observed within minutes. The suspension was stirred at room temperature for 48 hours and the cloudy, heterogeneous reaction mixture was noted to be slightly yellowed. The suspension was diluted with a mixture of hexanes:EtOAc (1:1), the slurry filtered through a short plug of Celite® to remove the triethylammonium salt, the filtrate concentrated under reduced pressure, and the residue redissolved in a mixture of hexanes:EtOAc (1:1). Chromatography (SiO$_2$, 1:1 hexanes:ethyl acetate) via MPLC yielded the title compound as a white, crystalline solid (31.1 mg, 0.0294 mmol, 64.7%). If necessary, residual EtOAc was removed by storage under high vacuum for ≥24 h. $^1$H NMR (500 MHz, CDCl$_3$): δ 8.11 (dd, J=8.5, 1.4 Hz, 2H, C2O$_2$C-o-Ph), 7.79 (dd, J=8.4, 1.3 Hz, 2H, C3'NHCO-o-Ph), 7.62 (tt, J=7.6, 1.3 Hz, 1H, C2O$_2$C-p-Ph, 1H), 7.55-7.47 (m, 3H, C2O$_2$C-m-Ph and C3'NHCO-p-Ph), 7.44-7.35 (m, 6H, C3'-o-Ph, C3'-m-Ph and C3'NHCO-m-Ph), 7.27 (tt, J=7.0, 1.7 Hz, 1H, C3'-p-Ph), 7.17 (d, J=8.5 Hz, 1H, C3'NH), 6.28 (s, 1H, H10), 6.19 (br dd, J=9, 9 Hz, 1H, H13), 5.69 (dd, J=8.5, 3.6 Hz, 1H, H3'), 5.68 (d, J=6.7 Hz, 1H, H2), 4.98 (d, J=3.6 Hz, 1H, H2'), 4.96 (dd, J=9.7, 2.4 Hz, 1H, H5), 4.44 (ddd, J=10.9, 6.6, 4.1 Hz, 1H, H7), 4.31 (d, J=8.4 Hz, 1H, H20α), 4.20 (d, J=8.4 Hz, 1H, H20β), 4.13 {sept, J=6.1 Hz, 3H, C2'OSi[OCH(CH$_3$)$_2$]$_3$}, 3.80 (d, J=7.1 Hz, 1H, H3), 2.56 (ddd, J=14.8, 9.8, 6.6 Hz, 1H, H6α), 2.47 (d, J=4.1 Hz, 1H, C7OH), 2.42 (s, 3H, C4OAc), 2.29 (dd, J=15.4, 9.4 Hz, 1H, H14α), 2.24 (s, 3H, C10OAc), 2.06 (dd, J=15.4, 8.9 Hz, 1H, H14β), 1.91 (d, J=1.4 Hz, 3H, C18H$_3$), 1.88 (ddd, J=14.3, 11.0, 2.4 Hz, 1H, H6β), 1.76 (br s, 1H, C1OH), 1.68 (s, 3H, C19H$_3$), 1.23 (s, 3H, C17H$_3$), 1.15 {d, J=6.1 Hz, 9H, C2'OSi[OCH(CH$_3$)$_a$(CH$_3$)$_b$]$_3$}, 1.12 {d, J=6.1 Hz, 9H, C2'OSi[OCH(CH$_3$)$_a$(CH$_3$)$_b$]$_3$}, and 1.12 (s, 3H, C16H$_3$). $^{13}$C NMR (125 MHz, CDCl$_3$): δ 204.1, 171.5, 171.1, 170.1, 167.3, 167.2, 143.1, 138.3, 134.4, 133.9, 132.9, 131.9, 130.4, 129.4, 128.9 (×2), 128.8, 128.1, 127.3, 127.0, 84.7, 81.2, 79.3, 76.7, 75.9, 75.3, 74.9, 72.3, 71.5, 66.7, 58.7, 55.8, 45.7, 43.4, 35.8, 35.7, 27.0, 25.44, 25.42, 23.0, 22.4, 21.1, 15.2, and 9.8. HRMS (ESI) Calcd for C$_{56}$H$_{71}$NNaO$_{17}$Si [M+Na]$^+$1080.4383. found 1080.4380. IR (thin film) 3500 (br), 2974, 2934, 1729, 1666, 1603, 1583, 1515, 1485, 1452, 1371, 1313, 1269, 1241, 1174, 1114, 1052, 985, 897, 850, 800, 773, and 712 cm$^{-1}$. mp=126-129° C. TLC R$_f$ (1:1 Hexanes:EtOAc)=0.45.

Example 5

Preparation of 2'-O-(di-t-butyl ethyl orthosilyl)paclitaxel (1d)

Paclitaxel (49.3 mg, 0.0577 mmol, 1.0 equiv) was dissolved in dry THF (1.0 mL) in an oven-dried culture tube with a Teflon-lined cap and magnetic stir bar. Pyridine (0.12 mL, 1.48 mmol, 26 equiv) was added by syringe. A distilled sample of di-t-butoxydichlorosilane (0.349 mg, 1.42 mmol, 25 equiv) was added by Wiretrol®. The culture tube was sealed and the solution was allowed to stir at room temperature. A small amount of a white precipitate was observed after ca. 30 minutes, and the reaction mixture was noted to be cloudy and heterogeneous after stirring for 6 hours. To the suspension, pyridine was again added (0.47 mL, 5.81 mmol, 100 equiv). Immediately afterward, anhydrous ethanol (dried overnight over 3 Å molecular sieves, 0.68 mL, 11.7 mmol, 200 equiv) was added. The mixture was allowed to stir for one additional hour at room temperature. Analysis of the crude mixture was completed by removing a 0.1 mL aliquot of the reaction solution, removing the volatile components under reduced pressure, and analyzing the crude $^1$H NMR spectrum. The results indicated that the reaction was complete. The remainder of the reaction suspension was diluted with a mixture of hexanes:EtOAc (1:1), the slurry filtered through a short plug of Celite® to remove the pyridinium salt, the filtrate concentrated under reduced pressure, and the residue redissolved in a mixture of hexanes:EtOAc (2:1). Chromatography (SiO$_2$, 2:1 hexanes:EtOAc) via MPLC yielded the title compound as a white, crystalline solid (52.0 mg, 0.0485 mmol, 84.1%). If necessary, residual EtOAc was removed by storage under high vacuum for ≥24 h. $^1$H NMR (500 MHz, CDCl$_3$): δ 8.11 (dd, J=8.5, 1.4 Hz, 2H, C2O$_2$C-o-Ph), 7.79 (dd, J=8.4, 1.4 Hz, 2H, C3'NHCO-o-Ph), 7.62 (tt, J=7.4, 1.3 Hz, 1H, C2O$_2$C-p-Ph, 1H), 7.56-7.46 (m, 3H, C2O$_2$C-m-Ph and C3'NHCO-p-Ph), 7.45-7.33 (m, 6H, C3'-o-Ph, C3'-m-Ph and C3'NHCO-m-Ph), 7.30-7.22 (m, 1H, C3'-p-Ph), 7.15 (d, J=8.4 Hz, 1H, C3'NH), 6.28 (s, 1H, H10), 6.18 (br dd, J=9, 9 Hz, 1H, H13), 5.68 (d, J=7.2 Hz, 1H, H2), 5.66 (dd, J=8.3, 3.6 Hz, 1H, H3'), 5.01 (d, J=3.6 Hz, 1H, H2'), 4.97 (dd, J=9.7, 2.3 Hz, 1H, H5), 4.44 (ddd, J=10.8, 6.6, 4.1 Hz, 1H, H7), 4.31 (d, J=8.4 Hz, 1H, H20α), 4.19 (d, J=8.4 Hz, 1H, H20β), 3.79 (d, J=7.0 Hz, 1H, H3), 3.64 (q, J=7.0 Hz, 2H, C2'OSiOCH$_2$CH$_3$), 2.56 (ddd, J=14.8, 9.7, 6.6 Hz, 1H, H6α), 2.45 (d, J=4.1 Hz, 1H, C7OH), 2.41 (s, 3H, C4OAc), 2.28 (dd, J=15.4, 9.4, Hz, 1H, H14α), 2.24 (s, 3H, C10OAc), 2.05 (dd, J=15.3, 9.0 Hz, 1H, H14β), 1.90 (d, J=1.4 Hz, 3H, C18H$_3$), 1.88 (ddd, J=14.4, 11.1, 2.5 Hz, 1H, H6β), 1.68 (s, 4H, C1OH and C19H$_3$), 1.26 (s, 9H, C2'OSiOC(CH$_3$)$_2$], 1.25 (s, 9H, C2'OSiOC(CH$_3$)$_2$], 1.23 (s, 3H, C17H$_3$), and 1.13 (overlapping t, J=7.0 Hz, 3H, C2'OSiCH$_2$CH$_3$ and s, 3H, C16H$_3$). $^{13}$C NMR (125 MHz, CDCl$_3$): δ 204.1, 171.5, 171.0, 170.0, 167.3, 167.2, 143.1, 138.4, 134.4, 133.9, 132.8, 131.9, 130.4, 129.4, 128.90, 128.89, 128.8, 128.1, 127.3, 127.0, 84.7, 81.2, 79.3, 76.6, 75.9, 75.3, 74.9, 73.99, 73.98, 72.3, 71.4, 59.3, 58.7, 55.8, 45.7, 43.4, 35.8, 35.7, 31.41, 31.38, 27.0, 22.9, 22.3, 21.1, 18.2, 15.1, and 9.8. IR (thin film) 3500 (br), 2976, 2936, 1726, 1665, 1603, 1582, 1514, 1485, 1452, 1389, 1368, 1312, 1270, 1242, 1179, 1128, 1069, 1025, 981, 909, 853, 821, 800, 775, 733, and 711 cm$^{-1}$. HRMS (ESI) Calcd for $C_{57}H_{73}NNaO_{17}Si$ [M+Na]$^{+}$ 1094.4540; found 1094.4579. mp=130-134° C. TLC $R_f$ (2:1 Hexanes:EtOAc)=0.2.

Example 6

Preparation of 2',7-Di-O-(tri-n-octyl orthosilyl)paclitaxel (2b)

Paclitaxel (57.8 mg, 0.0677 mmol, 1.0 equiv) was dissolved in dry THF (1.5 mL) in an oven-dried culture tube fitted with a Teflon-lined cap and magnetic stir bar. Pyridine (25 μL, 0.309 mmol, 4.6 equiv) was added by Wiretrol®. A 1.67:1 mixture of tri-n-octyloxychlorosilane:tetra-n-octyloxysilane (0.155 mg, 0.199 mmol, 2.9 equiv of tri-n-octyloxychlorosilane) was added, and formation of a white precipitate was immediately observed. The culture tube was sealed and the suspension was allowed to stir for 5 h at room temperature. The reaction mixture was diluted with a mixture of hexanes:EtOAc (1:1), and the slurry filtered through a short plug of Celite® to remove the pyridinium salt. The filtrate was concentrated under reduced pressure, and the residue purified by MPLC (SiO$_2$, 9:1 hexanes:EtOAc) to yield 2b as a viscous oil (88.1 mg, 0.0523 mmol, 77.3%). Additional elution in hexanes:EtOAc (2:1) yielded 1b (1.7 mg, 0.0013 mmol, 2.0%). If necessary, residual EtOAc was removed from 2b by storage under high vacuum for ≥24 h. $^1$H NMR (500 MHz, CDCl$_3$): δ 8.13 (dd, J=8.6, 1.4 Hz, 2H, C2O$_2$C-o-Ph), 7.78 (dd, J=8.6, 1.5 Hz, 2H, C3'NHCO-o-Ph), 7.60 (tt, J=7.4, 1.2 Hz, 1H, C2O$_2$C-p-Ph, 1H), 7.54-7.46 (m, 3H, C2O$_2$C-m-Ph and C3'NHCO-p-Ph), 7.44-7.35 (m, 6H, C3'-o-Ph, C3'-m-Ph and C3'NHCO-m-Ph), 7.28 (tt, J=7.2, 1.3 Hz, 1H, C3'-p-Ph), 7.22 (d, J=8.7 Hz, 1H, C3'NH), 6.55 (s, 1H, H10), 6.23 (br dd, J=10, 9 Hz, 1H, H13), 5.74 (dd, J=8.6, 3.0 Hz, 1H, H3'), 5.70 (d, J=7.1 Hz, 1H, H2), 4.99 (d, J=3.0 Hz, 1H, 2'H), 4.94 (dd, J=9.7, 1.9 Hz, 1H, H5), 4.61 (dd, J=10.6, 6.8 Hz, 1H, H7), 4.31 (d, J=8.4 Hz, 1H, H20α), 4.20 (d, J=8.4 Hz, 1H, H20β), 3.86 (d, J=7.0 Hz, 1H, H3), 3.67 {t, J=6.7 Hz, 6H, C7OSi[OCH$_2$(CH$_2$)$_6$CH$_3$]$_3$}, 3.61 {t, J=6.7 Hz, 6H, C2'OSi[OCH$_2$(CH$_2$)$_6$CH$_3$]$_3$}, 2.65 (ddd, J=14.7, 9.7, 6.8 Hz, 1H, H6α), 2.45 (s, 3H, C4OAc), 2.33 (dd, J=15.3, 9.4 Hz, 1H, H14α) 2.13 (s, 3H, C10OAc),), 2.06 (d, J=1.2 Hz, 3H, C18H$_3$), 2.09-2.02 (m, 1H, H14β), 1.96 (ddd, J=14.5, 10.8, 2.2 Hz, 1H, H6β), 1.73 (s, 3H, C19H$_3$), 1.66 (br s, 1H, C1OH), 1.56-1.44 {m, 12H, C2'OSi[OCH$_2$CH$_2$(CH$_2$)$_5$CH$_3$]$_3$ and C7OSi[OCH$_2$CH$_2$(CH$_2$)$_5$CH$_3$]$_3$}, 1.34-1.21 {m, 63H, C17H$_3$, C2'OSi[OCH$_2$CH$_2$(CH$_2$)$_5$CH$_3$]$_3$, and C7OSi[OCH$_2$CH$_2$(CH$_2$)$_5$CH$_3$]$_3$}, 1.17 (s, 3H, C16H$_3$), and 0.88 {overlapping t's, J=6.8 Hz, 18H, C2'OSi[OCH$_2$CH$_2$(CH$_2$)$_5$CH$_3$]$_3$ and C7OSi[OCH$_2$CH$_2$(CH$_2$)$_5$CH$_3$]$_3$}. $^{13}$C NMR (75 MHz, CDCl$_3$): δ 202.4, 170.9, 169.8, 168.7, 167.3, 167.2, 140.9, 138.3, 134.3, 133.8, 133.3, 131.9, 130.4, 129.4, 128.91, 128.89, 128.8, 128.1, 127.3, 126.8, 84.6, 81.2, 79.0, 76.8, 75.8, 75.1, 74.9, 72.0, 71.5, 64.1, 63.9, 58.3, 55.5, 46.8, 43.5, 36.6, 35.6, 32.5, 32.4, 32.1, 32.0, 29.6, 29.63, 29.60, 29.57, 26.7, 25.92, 25.89, 23.0, 22.91, 22.90, 21.6, 21.1, 14.3 (×2), 14.1, and 10.4. HRMS (ESI) Calcd for $C_{95}H_{151}NNaO_{20}Si_2$ [M+Na]$^{+}$1705.0260. found 1705.0228. IR (thin film) 3500 (br), 2927, 2856, 1728, 1741, 1721, 1634, 1580, 1545, 1456, 1371, 1315, 1270, 1239, 1174, 1095, 1028, 989, 968, 924, 893, 843, 779, and 709 cm$^{-1}$. TLC $R_f$ (3:1 Hexanes:EtOAc) =0.55.

Example 7

Preparation of 7-O-(triethyl orthosilyl)paclitaxel (3a)

Bis-silicate ester 2a (99.5 mg, 0.0845 mmol, 1.0 equiv) was dissolved in d$_6$-acetone (1.8 mL, dried over 3 Å molecular sieves) in an NMR tube. A 9:1 mixture of D$_2$O:TFA was added (200 μL) and the reaction progress was monitored by $^1$H NMR spectroscopy. After eight minutes at 21.4° C., the mixture was transferred into saturated aqueous NaHCO$_3$ (2 mL). This mixture was extracted with CH$_2$Cl$_2$ (3×5 mL). The combined organic extracts were dried over MgSO$_4$. and concentrated under reduced pressure. The residue was purified by MPLC (SiO$_2$, 2:1 hexanes:EtOAc) to provide recovered starting material 2a (27.3 mg, 0.0232 mmol, 27.4%). Additional elution in 1:1 hexanes:EtOAc gave the title compound as a white, crystalline solid [56.9 mg, 0.0560 mmol, 66.3% (91.4% brsm)]. If necessary, residual EtOAc was removed by storage under high vacuum for ≥24 h. $^1$H NMR (500 MHz, CDCl$_3$): δ 8.12 (dd, J=8.5, 1.3 Hz, 2H, C2O$_2$C-o-Ph), 7.75 (dd, J=8.5, 1.4 Hz, 2H, C3'NHCO-o-Ph), 7.61 (tt, J=7.5, 1.2 Hz, 1H, C2O$_2$C-p-Ph, 1H), 7.53-7.46 (m, 5H, C2O$_2$C-m-Ph, C3'NHCO-p-Ph, and C3'-o-Ph,), 7.43-7.37 (m, 4H, C3'-m-Ph and C3'NHCO-m-Ph), 7.34 (tt, J=7.3, 1.2 Hz, 1H, C3'-p-Ph), 7.09 (d, J=9.0 Hz, 1H, C3'NH), 6.56 (s, 1H, H10), 6.18 (br dd, J=9, 9 Hz, 1H, H13), 5.80 (dd, J=6.9, 2.5 Hz, 1H, H3'), 5.69 (d, J=6.9 Hz, 1H, H2), 4.93 (dd, J=9.6, 1.7 Hz, 1H, H5), 4.78 (dd, J=4.9, 2.7 Hz, 1H, 2'H), 4.57 (dd, J=10.5, 6.9 Hz, 1H, H7), 4.30 (d, J=8.4 Hz, 1H, H20α), 4.19 (dd, J=8.3, 0.9 Hz, 1H, H20β), 3.83 (d, J=6.9 Hz, 1H, H3), 3.76 [q, J=7.0 Hz, 6H, C7OSi(OCH$_2$CH$_3$)$_3$], 3.69 (br s, 1H, C2'OH), 2.65 (ddd, J=14.7, 9.7, 6.9 Hz, 1H, H6α), 2.37 (s, 3H, C4OAc), 2.35-2.25 (m, 2H, H14α and H14β), 2.15 (s, 3H, C10OAc), 1.95 (ddd, J=14.6, 10.7, 2.1 Hz, 1H, H6β), 1.93 (d, J=1.3 Hz, 3H, C18H$_3$), 1.76 (br s, 1H, C1OH), 1.73 (s, 3H, C19H$_3$), 1.23 (s, 3H, C17H$_3$), 1.19 [t, J=7.0 Hz, 9H, C7OSi(OCH$_2$CH$_3$)$_3$], and 1.16 (s, 3H, C16H$_3$). $^{13}$C NMR (125 MHz, CDCl$_3$): δ 202.4, 172.6, 170.4, 169.0, 167.2, 167.1, 140.1, 138.2, 133.9, 133.8, 132.1, 130.3, 129.4, 129.1, 128.89, 128.87, 128.5, 127.3, 127.24, 127.23, 84.4, 81.5, 78.8, 76.8, 76.1, 74.8, 73.4, 72.5, 72.1, 59.5, 58.6, 55.0, 47.0, 43.4, 36.7, 35.6, 26.8, 22.9, 21.1, 21.0, 18.2, 14.5, and 10.3. HRMS (ESI) Calcd for $C_{53}H_{65}NNaO_{17}Si$ [M+Na]$^{+}$1038.3914. found 1038.3914. IR (thin film) 3500 (br), 2975, 2898, 1724, 1653, 1602, 1580, 1515, 1485, 1451, 1394, 1370, 1314, 1266, 1240, 1172, 1079, 1025, 969, 913, 888, 839, 797, and 712 cm$^{-1}$. mp=141-146° C. TLC $R_f$ (1:1 Hexanes:EtOAc)=0.5.

Example 8

Preparation of 7-O-(tri-n-octyl orthosilyl)paclitaxel (3b)

Bis-silicate ester 2b (88.1 mg, 0.0523 mmol, 1.0 equiv) was dissolved in d$_6$-acetone (1.8 mL, dried over 3 Å molecular sieves) in an NMR tube. A 9:1 mixture of D$_2$O:TFA was added (200 μL) and the solution became white and cloudy. Upon vigorous mixing for 30 seconds, the mixture became homogeneous and transparent. The hydrolysis progress was monitored by $^1$H NMR spectroscopy. After 30 minutes at room temperature, the solution was transferred into saturated aqueous NaHCO$_3$ (2 mL). This mixture was extracted with CH$_2$Cl$_2$ (3×5 mL). The combined organic layers were dried over MgSO₄ and concentrated under reduced pressure. The residue was purified by MPLC (SiO₂, 3:1 hexanes:EtOAc) to provide recovered 2b (12.9 mg, 0.0076 mmol, 27.4%). Additional elution in 2:1 hexanes:EtOAc gave the title compound as a crystalline solid [37.3 mg, 0.0294 mmol, 56.2% (65.7% brsm)]. If necessary, residual EtOAc was removed by storage under high vacuum for ≥24 h. $^1$H NMR (500 MHz, CDCl₃): δ 8.12 (dd, J=8.5, 1.3 Hz, 2H, C2O₂C-o-Ph), 7.75 (dd, J=8.5, 1.4 Hz, 2H, C3'NHCO-o-Ph), 7.61 (tt, J=7.4, 1.3 Hz, 1H, C2O₂C-p-Ph, 1H), 7.53-7.47 (m, 5H, C2O₂C-m-Ph, C3'NHCO-p-Ph, and C3'-o-Ph,), 7.43-7.38 (m, 4H, C3'-m-Ph and C3'NHCO-m-Ph), 7.34 (tt, J=7.2, 1.3 Hz, 1H, C3'-p-Ph), 7.06 (d, J=9.0 Hz, 1H, C3'NH), 6.53 (s, 1H, H10), 6.17 (br dd, J=9, 9 Hz, 1H, H13), 5.81 (dd, J=6.8, 2.4 Hz, 1H, H3'), 5.68 (d, J=6.9 Hz, 1H, H2), 4.92 (dd, J=9.6, 1.8 Hz, 1H, H5), 4.78 (dd, J=4.8, 2.6 Hz, 1H, 2'H), 4.56 (dd, J=6.7, 10.5 Hz, 1H, H7), 4.29 (d, J=8.3 Hz, 1H, H20α), 4.19 (d, J=8.5 Hz, 1H, H20β), 3.83 (d, J=7.0 Hz, 1H, H3), 3.66 {t, J=6.7 Hz, 6H, C7OSi[OCH₂(CH₂)₆CH₃]₃}, 3.60 (d, J=4.9 Hz, 1H, C2'OH), 2.64 (ddd, J=14.7, 9.7, 6.9 Hz, 1H, H6α), 2.37 (s, 3H, C4OAc), 2.34-2.27 (m, 2H, H14α and H14β), 2.14 (s, 3H, C10OAc), 1.97-1.90 (m, 4H, H6β and C18H₃), 1.74-1.70 (m, 4H, C1 OH and C19H₃), 1.52 {tt, J=6.8, 6.8 Hz, 6H, C7OSi[OCH₂CH₂(CH₂)₅CH₃]₃}, 1.34-1.22 {m, 33H, C17H₃ and C7OSi[OCH₂CH₂(CH₂)₅CH₃]₃}, 1.16 (s, 3H, C16H₃), and 0.88 {t, J=6.8 Hz, 9H, C7OSi[OCH₂CH₂(CH₂)₅CH₃]₃}. $^{13}$C NMR (125 MHz, CDCl₃): δ 202.2, 172.7, 170.3, 168.8, 167.2, 167.0, 140.0, 138.3, 133.93, 133.89, 132.1, 130.4, 129.4, 129.1, 128.9 (×3), 128.5, 127.3, 127.2, 84.5, 81.5, 78.8, 76.8, 76.0, 74.9, 73.3, 72.1, 63.9, 58.6, 54.9, 47.0, 43.4, 36.6, 35.6, 32.5, 32.1, 29.62, 29.57, 26.8, 25.9, 22.91, 22.88, 21.1, 21.0, 14.5, 14.3, and 10.3. HRMS (ESI) Calcd for C₇₁H₁₀₁NNaO₁₇Si [M+Na]⁺ 1290.6731; found 1290.6738.

IR (thin film) 3500 (br), 2926, 2855, 1732, 1710, 1673, 1602, 1582, 1452, 1396, 1370, 1317, 1281, 1269, 1241, 1179, 1093, 1025, 988, 968, 890, 844, 809, and 712 cm$^{-1}$. mp=69-73° C. TLC R$_f$ (2:1 Hexanes:EtOAc)=0.4.

Example 9

Preparation of a Representative Compounds of the Invention

Using a procedure similar to the one described in Example 1, the following compounds were also prepared.

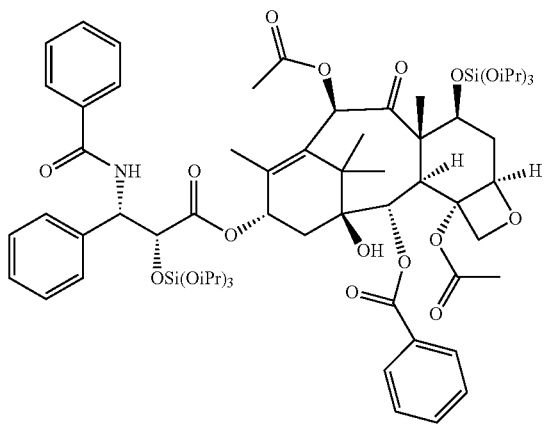

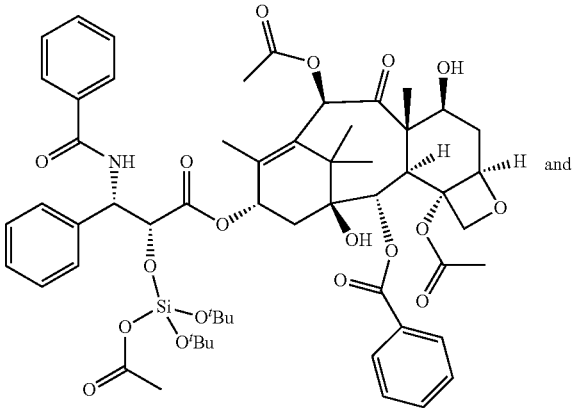

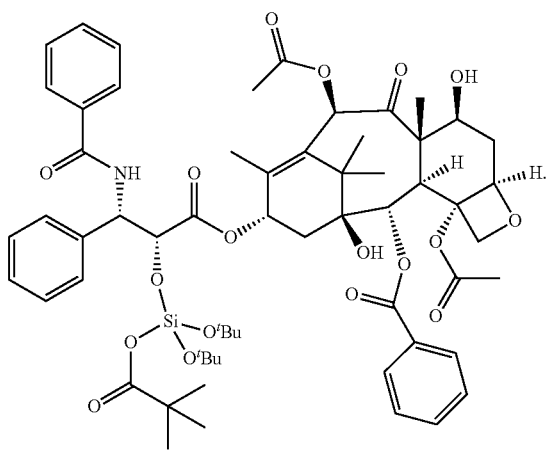

Example 10

Release Data

PTX silicate prodrug-loaded nanoparticles were prepared from Compounds 1a, 1b, 1c, 2a, 2b, and 4 as described herein (10 mg of PTX) and were dispersed in 10.0 ml Phosphate buffer solution at pH=7.4 or 6.4 in dialysis cassette (MW cutoff: 10 k) and incubated in a 37° C. shaker. At determined time intervals (1, 3, 6, 8 10, 24 hr), 250 μl nanosuspension (in triplicate) was removed from each cassette and freeze dried. Freeze dried samples were redissolved in acetonitrile and extracted overnight. HPLC was used to quantify the remaining prodrug in each cassette. Data for representative compounds of formula (I) is shown in FIG. 1, which shows paclitaxel silicate release data from nanoparticles. All the data points indicate silicate prodrug; Remaining % indicates the amount of prodrug that is still captured in nanoparticles in dialysis cassette.

Example 11

Cytotoxicity Against Tumor Cells In Vitro

Figure 2:
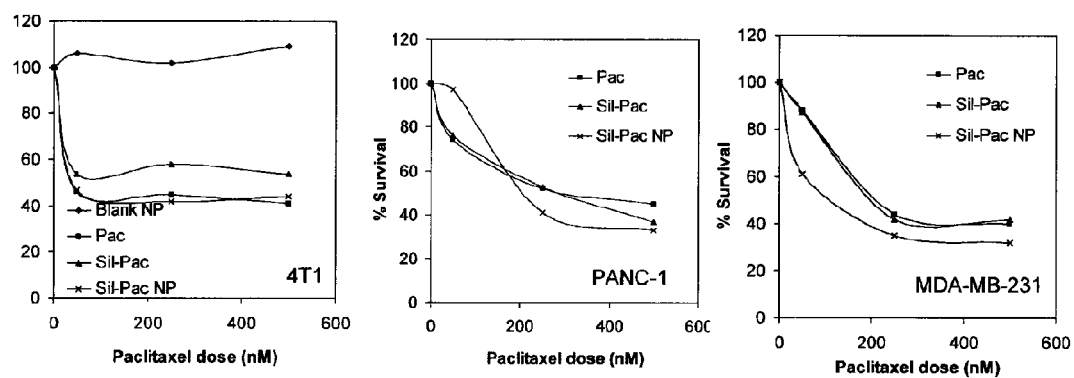
FIG. 2 Illustrates anticancer efficacy for representative compounds of formula (I) from Example 11.
Figure 3:
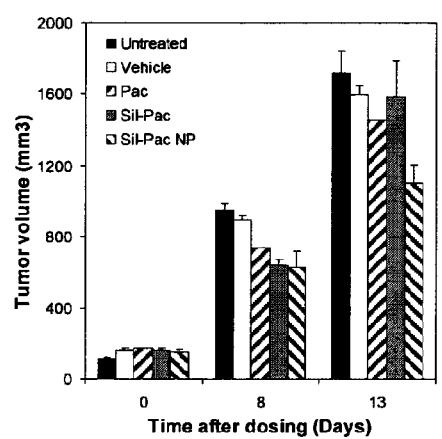
FIG. 3 Illustrates data for a representative compound of formula (I) from Example 12.

Tumor cells (4T1, PANC-1 or MDA-MB-231) were seeded in 96-well plates and allowed to attach. Cells were then treated with paclitaxel (solubilized in growth medium using ethanol), silicate prodrug (2a, solubilized in growth medium using ethanol), silicate prodrug nanoparticles (a 58:42 wt % mixture of the bis-triethyl silicate paclitaxel prodrug 2a and a 5K-10K PEG-PLGA BCP dispersed in growth medium) or copolymer-only (blank, no drug) nanoparticles for 72 hours. Cell viability was then measured using a standard MTS assay kit (Promega). As shown in FIG. 2 silicate prodrug and silicate prodrug nanoparticles demonstrated anticancer efficacy similar to the parent compound, paclitaxel. At the concentrations tested, blank particles did not have any effect on cell viability.

Example 12

4T1 Tumor Growth in Mice

Orthotopic 4T1 tumors were grown by injecting ~1×10$^6$ tumor cells in the mammary fat pad of BALB/c mice. When the tumors were about 100 mm$^3$ in volume, the animals were injected with a single dose of paclitaxel dissolved in 1:1 mix of ethanol and cremophor (same formulation as Taxol®), silicate prodrug (2a) dissolved in 1:1 mix of ethanol and cremophor (same formulation as Taxol®), or silicate prodrug nanoparticles dispersed in buffered saline. Untreated animals or those treated with just cremophor/ethanol vehicle were used as controls. Silicate prodrug nanoparticles resulted in greater tumor growth inhibition compared to the conventional paclitaxel treatment (1450±65 mm$^3$ Vs 1100±99 mm$^3$ on Day 13). Importantly, animals that received paclitaxel in cremophor/ethanol had severe tissue irritation and necrosis at the site of injection, whereas those that received the nanoparticle formulation had no inflammation. This study clearly indicates the benefit of formulating paclitaxel in the form of silicate prodrug nanoparticle formulation.

Examples 13-16

The properties and activity of a compound or a formulation of the invention can be evaluated using the assays described in Examples 13-16.

Example 13

PTX Silicate Hydrolysis Rates

A known quantity of a PTX prodrug was dissolved in 900 µL of d$_6$-acetone. To this homogenous solution, 100 µL of a 9:1 solution of D$_2$O: trifluoroacetic acid (TFA) was added, and the solution was vigorously mixed. The $^1$H NMR spectra was taken (16 transients) on a 500 MHz Varian instrument at multiple time points over the course of more than three half-lives. The study was conducted at room temperature (rt=22.5° C.±1.0° C.) Upon completion of the study, the 2' and/or 7 methine resonances were integrated in a baseline-adjusted NMR spectrum using MestRec software. The relative integrations were used to determine the extent of hydrolysis. The data from three replications was plotted on a semi-log scale to determine the k$_{obs}$ of the prodrug that were then converted to the k$_{rel}$ data as presented, defining the rate of the most slowly hydrolyzed prodrug (1d) as k$_{rel}$=1.0. Errors are defined as the standard deviation of the three trials.

$^1$H NMR spectroscopy was used to establish relative hydrolysis rates of compounds 1-3. The compounds were dissolved in a solution of d$_6$-acetone, D$_2$O, and trifluoroacetic acid (TFA) in a 90:9:1 ratio (v/v/v). Resonances of, e.g., H2' in the reactant silicate vs. product carbinol were monitored. No partially hydrolyzed silicate intermediates were detected, which suggests that the initial hydrolysis event (i.e., cleavage of the first Si—OR bond) is the rate-limiting step.

The results (Table 1) show that increasing the steric bulk of the silicate prodrug slows its hydrolysis rate. The k$_{rel}$ values differ by >2000× between the extremes of the triethyl PTX-silicate 1a to the hindered di-t-butyl/ethyl silicate 1d. The hydrolysis rates for 1a and 1b were similar (k$_{rel}$ of ca. 3), which shows that the hydrophobicity of the silicate can be significantly increased with only a small change in the relative hydrolysis rate. As a group, prodrugs bearing the silicate at C7 hydrolyzed ca. 10× slower than those at C2'.

TABLE 1

Hydrolysis rates of the PTX silicate prodrugs relative to that of the slowest (1 d).

| Prodrug | at C2' k$_{rel}$ | at C7 k$_{rel}$ |
| --- | --- | --- |
| 1a | 2200 ± 600 | n/a |
| 1b | 710 ± 30 | n/a |
| 1c | 69 ± 4 | n/a |
| 1d | 1.0 ± 0.1 | n/a |
| 2a | 1800 ± 100 | 250 ± 10[a] |
| 2b | 460 ± 10 | 41 ± 3[b] |
| 3a | n/a | 270 ± 10 |
| 3b | n/a | 55 ± 3 |

[a]The rate of hydrolysis of in situ generated 3a to PTX.
[b]The rate of hydrolysis of in situ generated 3b to PTX.

Example 14

In Vitro Cytotoxicity of PTX Silicate Prodrugs

MDA-MB-231 and MDA-MB-231 Luciferase positive cells were maintained independently in MEM supplemented with 1% pen/strep and 10% FBS at 37° C. in a humidified incubator. MDA-MB-231 cells were obtained from the American Type Culture Collection. MDA-MB-231 Luc+ cells were obtained from CaliperLS (Hopkinton, Mass., USA). For MTT cytotoxicity studies, MDA-MB-231 cells were seeded at 8,000 cells/well in a 96 well plate in 100 µL MEM with 5% FBS. Paclitaxel, and paclitaxel silicate prodrug stock solutions of 10 mM were prepared in DMSO. Stock solutions were diluted to 2× concentration in MEM with 5% FBS, 100 µL volume, and pipetted into the 96 well plate. Concentration ranges were from 1-10,000 nM. After 48 hours, 30 µL of MTT working reagent was added to cells. Absorbance at 490 nm was monitored on a 96 well plate UV vis detector at 60 minutes. IC50 values were determined by nonlinear regression analysis of log concentration v. response data obtained from the MTT assay. The IC50 was interpolated from the resulting curves using Graphpad Prism v5.1 (Graphpad Software Inc. La Jolla Calif., USA).

Cytotoxicity of the PTX silicate prodrugs 1-3 was examined in the MDA-MB-231 human breast cancer cell line (Table 2). With the exception of the two least hydrolytically labile prodrugs (1d and 3b), all of the silicates showed very similar growth inhibition properties to one another as well as to PTX itself.

TABLE 2

Cytotoxicity of silicate prodrugs 1-3 in MDA-MB-231 cells.[a]

| Compound | IC$_{50}$ (nM) |
|---|---|
| PTX | 23.6 (±9.8) |
| 1a | 23.0 (±10.7) |
| 1b | 35.6 (±19.4) |
| 1c | 24.5 (±12.7) |
| 1d | 8140. (±1320) |
| 2a | 74.4 (±35.0) |
| 3a | 21.4 (±12.5) |
| 3b | 540. (±113) |

[a]cell viability measured after 48 h.

Example 15

NP Formulation of Silicate 2a with PEG-b-PLGA by FNP

Prodrug 2a-loaded nanoparticles were fabricated by the Confined-Impingement Jets Mixer (see Johnson B K, Prud'homme R K, AIChE, 2003, 49:2264-2282). A 5K-10K PEG-b-PLGA polymer (25 mg) and prodrug 2a (35 mg) were dissolved in THF (2.5 ml) and impinged against 2.5 ml DI water in the CIJ mixer over the course of 5 s. The resulting nanoparticle suspension, was immediately diluted in 45 mL DI water, resulting in a nanosupension of 1.2 mg/mL in a mixture of THF and DI water (5:95). The nanosuspension was lyophilized (Freezone 4.5, Labconco) and kept frozen at −80° C. for long-term storage. After freeze drying, NPs were dispersed in DI water (~1 mg/ml, 0.1 wt %) while cooling in an ice bath using probe sonication (Sonicator 3000, Ultrasonic liquid processor) at 20 kHz for five minutes.

A hallmark of the FNP process is that enables the production of stable NPs that carry much higher drug loads than is typical for more conventional polymer-based carriers. The bis-triethoxysilicate prodrug 2a and PEG-b-PLGA (5K-10K) were formulated into nanoparticles (hereafter called 2a-NP) by FNP. The load level of the prodrug 2a was determined (HPLC) to be 47±5 wt % (equivalent to a 34 wt % of unfunctionalized PTX). This is unusually high for a drug delivery formulation of a member of the taxane family. DLS measurements of the 2a-NPs showed an average hydrodynamic diameter of 120 nm (S.D. of 10 nm for nine measurements—three measurements from each of three separate formulations). The initial average size was essentially maintained for at least three days. Cryo-TEM was used to obtain more information about the nanoscopic structures of these particles. Some images show the spherical nature of 2a-NPs, while others suggest a core-shell microstructure.

Example 16

PTX Silicate Prodrug NP Efficacy in Tumor-Bearing Animals

The in vivo efficacy of 2a-NPs was evaluated in mice carrying orthotopic MDA-MB-231 tumor xenografts. This cell line was stably transfected with luciferase to enable subsequent quantitative luminescence studies. The prodrug-loaded particles of 2a-NP were prepared for administration by lyophilization to remove the organic solvent and water immediately following preparation of the initial FNP dispersion. The resulting white powder was then resuspended into a PBS solution (1 wt %, probe tip sonication) immediately prior to injection into tumor-bearing animals.

Three active PTX agents were administered (n≥5 for each group): 2a-NP, PTX-CrEL® (formulated as in Taxol®), and Abraxane®. Equimolar quantities of PTX were used in each dosing regimen to enable comparison of the therapeutic response of 2a-NP vis-à-vis the current clinical formulations of PTX. Non-drug loaded CrEL® and PEG-b-PLGA NP (hereafter, blank NPs) control groups were also included.

Figure 5:
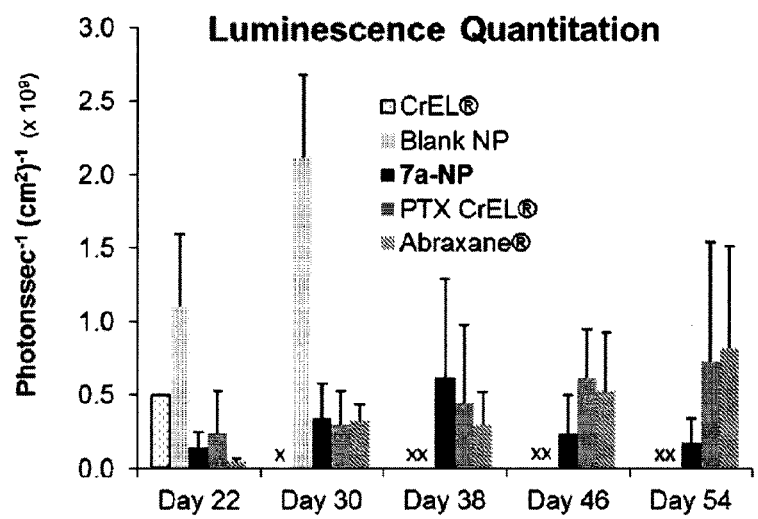
FIG. 5 Illustrates mean luminescence quantitation measured in Example 16.

Quantitative luminescence was used to determine therapeutic response. Luciferase-catalyzed oxidation of luciferin is an ATP-dependent reaction, and the intensity of the resulting photon emission was taken to be indicative of the number of viable grafted luc+MDA-MB-231 cells at the primary tumor site. The data in FIG. 5 summarize the luminescence response from all animals in a given test group at the indicated time points. Highlights are that each of the 2a-NP, PTX-CrEL®, and Abraxane® treatment groups showed significant inhibition of tumor growth relative to the control groups and that all three of 2a-NP, PTX-CrEL®, and Abraxane® were statistically comparable in their protective capacity. It is important to restate that the dosage of PTX or PTX prodrug was identical (50 µmol kg$^{-1}$) for all treatment groups and that, because the wt % of prodrug in 2a-NP (47±5 wt %) was considerably higher than that of PTX in PTX-CrEL® (1.1%) or Abraxane® (10%), much lower amounts of excipient were administered to the animals receiving 2a-NPs. The data also suggest that tumors in mice treated with 2a-NPs were decellularized (i.e., less dense at the tumor core) relative to Abraxane®- and PTX-CrEL®-treated mice. Histologic assessment of tumors at the study endpoint revealed a central necrotic/apoptotic core in all PTX treatment groups. Hematoxylin and eosin (H&E) staining of tumors showed an outer rim of mitotically active cells with a large central core that stained positive for caspase-3, a marker for apoptosis. A trend towards a larger central non-viable core was observed in the 2a-NP group relative to the PTX-CrEL® and Abraxane® treatment groups, thus providing additional evidence for greater decellularization of tumors in mice treated with 2a-NPs.

Upon conclusion of the luminescence study, the toxicological profile was determined for the 2a-NP, PTX-CrEL® and Abraxane® treatment groups (Table 3). Qualitatively, tail tissue near the injection site in the CrEL®- and PTX-CrEL®-treated mice were found to exhibit necrotic characteristics, suggesting significant toxic side effects from the CrEL® excipient. Plasma solute assay and enzymology were used to assess hepatotoxicity. Notably, in Abraxane®-treated mice, mean aspartate transaminase (AST) and alanine transaminase (ALT) levels were above normal (vs. Balb/c nude mice), suggesting potentially greater liver damage. Lymphocytopenia was noted in both the Abraxane® and PTX-CrEL® groups, while values for 2a-NP-treated mice fell within the normal range. The absence of hematological or liver toxicity are encouraging and consistent with the idea that 2a-NP provides lower levels of toxic agent over a longer duration by virtue of slow release of PTX, thereby leading to a better safety profile, while maintaining equivalent efficacy to current clinical formulations.

TABLE 3

Selected toxicological profile data for PTX-CrEL ®, Abraxane ®, and 2a-NP groups.

| Treatment | ALT (U/L) | AST (U/L) | Mean Cell Hemoglobin (g · dL$^{-1}$) | Lymphocytes (%) | Neutrophils (%) |
|---|---|---|---|---|---|
| Expected | 51.3 (±18.8) | 119.4 (±95.5) | 30.4 (±2.7) | 62.5 (±10.3) | 29.9 (±8.4) |
| Untreated | 27.3 (±6.3) | 194.2 (±71.2) | | | |
| 2a-NP | 24.3 (±9.0) | 123.6 (±61.1) | 27.6 (±0.6) | 59.7 (±16.2) | 32.0 (±13.0) |
| PTX-CrEL ® | 27.2 (±3.8) | 170.0 (±69.2) | 27.9 (±3.3) | 43.7 (±5.0) | 46.7 (±2.1) |
| Abraxane ® | 89.0 (±79.2) | 361.6 (±187.8) | 30.5 (±1.7) | 46.0 (±21.1) | 49.0 (±23.5) |

The efficacy of a new class of PTX silicate prodrugs has been established. The strategy relies upon the ability to control both the hydrophobicity and the hydrolysis rate of these prodrugs. Each of these features provides a mechanism for enhancing drug encapsulation and release properties when the prodrugs are encapsulated in nanoparticles. Rates of hydrolysis of the prodrugs via $^1$H NMR spectroscopic analysis were determined. Cytotoxicity studies were performed. Prodrugs 1a-c, 2a, and 3a all showed IC$_{50}$ values similar to that of the parent PTX. Silicate prodrug 2a was formulated via FNP to provide nanoparticles 2a-NP, which contained very with high levels (47±5 wt %) of prodrug load. Cryoscopic transmission electron microscopy suggested a core-shell nature for these particles. Tumor-bearing mouse models were dosed with three taxane-containing agents, and quantitative luminescence was used to assess comparative in vivo antitumor efficacy. The 2a-NPs were found to display similar effectiveness as the clinically used formulations PTX-CrEL® and Abraxane®. Importantly, liver and blood toxicology and histology studies showed that the 2a-NP treatment group demonstrated minimal toxicity. Notably, the amount of excipient used in the 2a-NP formulations is significantly lower than that in the PTX-CrEL® and Abraxane® drugs.

Example 17

The following illustrate representative pharmaceutical dosage forms, containing a compound of the invention ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound comprising a taxane linked to one or more groups of formula (I):

—Si(OR)$_3$     (I)

wherein:

each R is independently selected from (C$_1$-C$_{20}$)alkanoyl, (C$_2$-C$_{20}$)alkenylcarbonyl, (C$_2$-C$_{20}$)alkynylcarbonyl, wherein each (C$_1$-C$_{20}$)alkanoyl, (C$_2$-C$_{20}$)alkenylcarbonyl, and (C$_2$-C$_{20}$)alkynylcarbonyl, is optionally substituted with one or more hydroxy, (C$_1$-C$_6$)alkoxy, oxo, halo, or aryl.

2. The compound of claim 1 wherein the taxane is a paclitaxel or docetaxel.

3. A compound of formula (Ia):

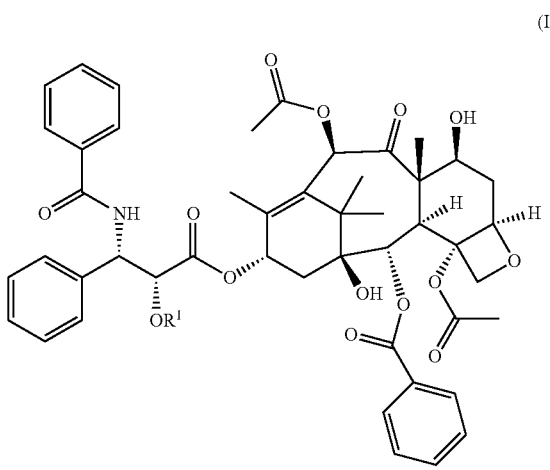

wherein R¹ is a group of formula (I),

—Si(OR)₃ (I)

wherein:
each R is independently selected from $(C_1-C_{20})$alkyl, $(C_2-C_{20})$alkenyl, $(C_2-C_{20})$alkynyl, $(C_1-C_{20})$alkanoyl, $(C_2-C_{20})$alkenylcarbonyl, and $(C_2-C_{20})$alkynylcarbonyl, wherein each $(C_1-C_{20})$alkyl, $(C_2-C_{20})$alkenyl, $(C_2-C_{20})$alkynyl, $(C_1-C_{20})$alkanoyl, $(C_2-C_{20})$alkenylcarbonyl, and $(C_2-C_{20})$alkynylcarbonyl, is optionally substituted with one or more hydroxy, $(C_1-C_6)$alkoxy, oxo, halo, or aryl;
or a salt thereof.

4. A compound of formula (Ib):

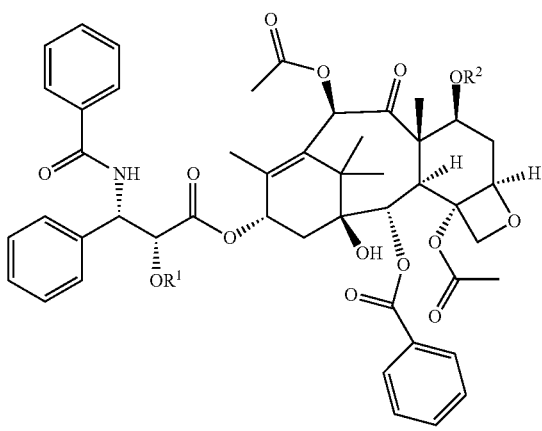

wherein R¹ and R² are each independently a group of formula (I),

—Si(OR)₃ (I)

wherein:
each R is independently selected from $(C_1-C_{20})$alkyl, $(C_2-C_{20})$alkenyl, $(C_2-C_{20})$alkynyl, $(C_1-C_{20})$alkanoyl, $(C_2-C_{20})$alkenylcarbonyl, and $(C_2-C_{20})$alkynylcarbonyl, wherein each $(C_1-C_{20})$alkyl, $(C_2-C_{20})$alkenyl, $(C_2-C_{20})$alkynyl, $(C_1-C_{20})$alkanoyl, $(C_2-C_{20})$alkenyl-carbonyl, and $(C_2-C_{20})$alkynylcarbonyl, is optionally substituted with one or more hydroxy, $(C_1-C_6)$alkoxy, oxo, halo, or aryl;
or a salt thereof.

5. A compound of formula (Ic):

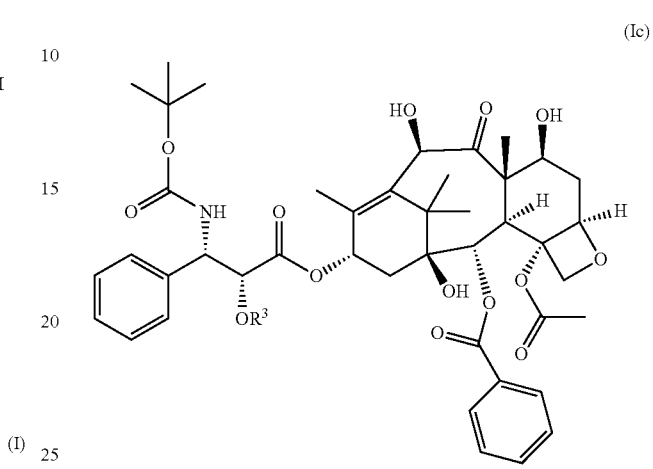

wherein R³ is a group of formula (I),

—Si(OR)₃ (I)

wherein:
each R is independently selected from $(C_1-C_{20})$alkyl, $(C_2-C_{20})$alkenyl, $(C_2-C_{20})$alkynyl, $(C_1-C_{20})$alkanoyl, $(C_2-C_{20})$alkenylcarbonyl, and $(C_2-C_{20})$alkynylcarbonyl, wherein each $(C_1-C_{20})$alkyl, $(C_2-C_{20})$alkenyl, $(C_2-C_{20})$alkynyl, $(C_1-C_{20})$alkanoyl, $(C_2-C_{20})$alkenyl-carbonyl, and $(C_2-C_{20})$alkynylcarbonyl, is optionally substituted with one or more hydroxy, $(C_1-C_6)$alkoxy, oxo, halo, or aryl;
or a salt thereof.

6. A compound selected from:

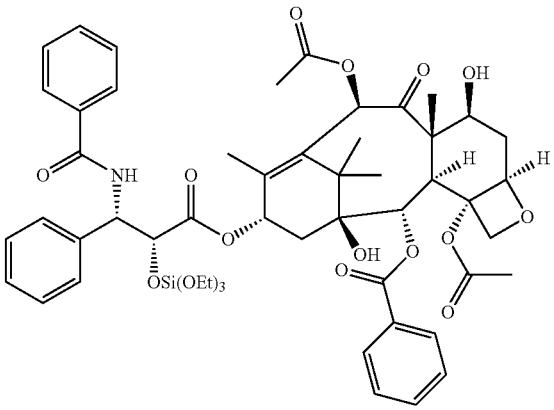

1a

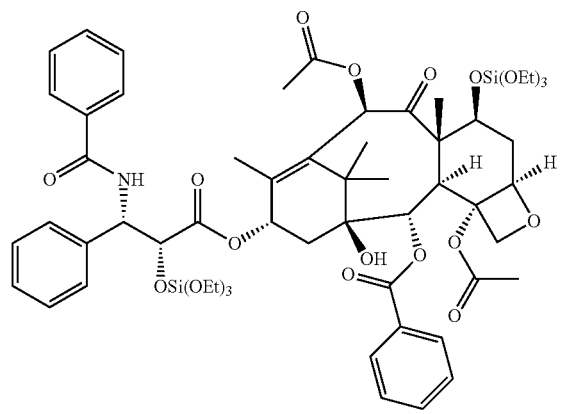
2a
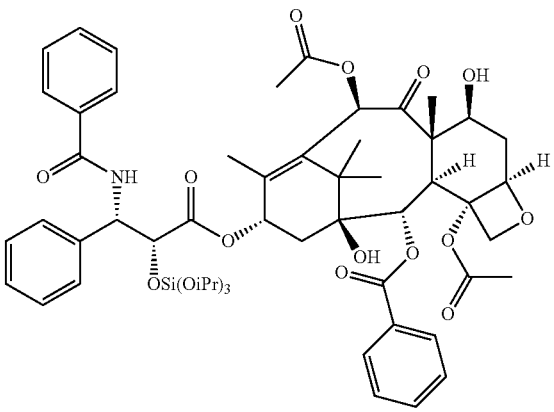
1c
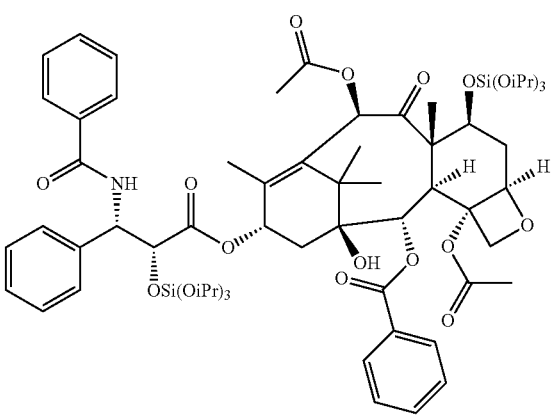
1b
4
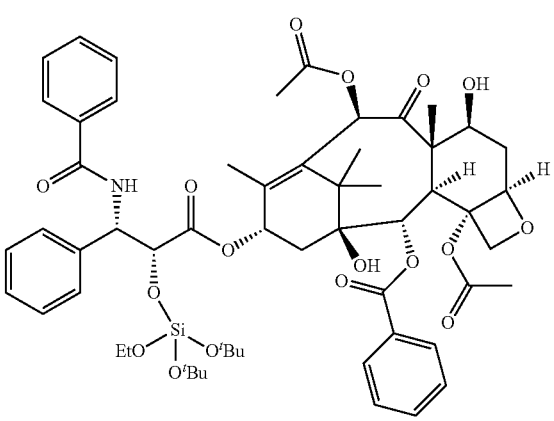
2b
1d

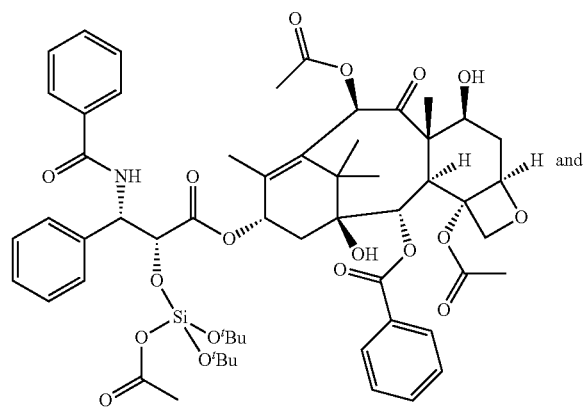
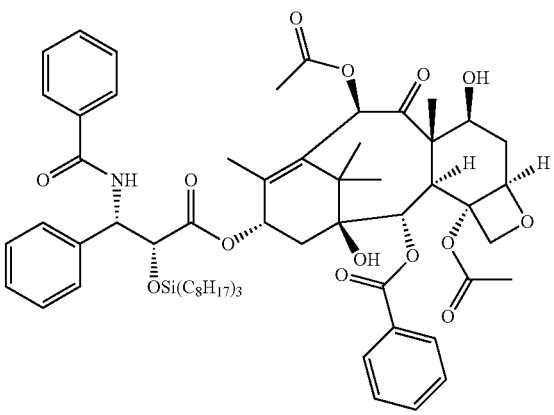
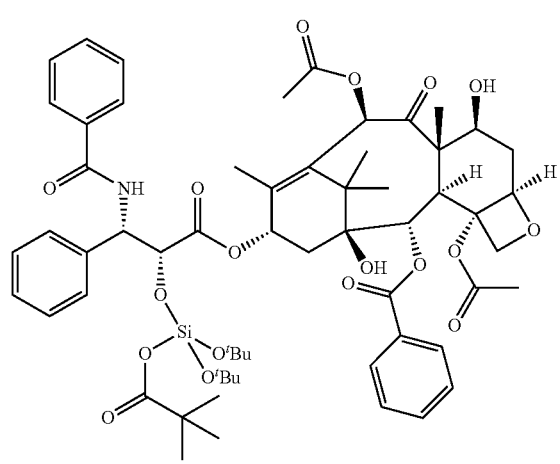
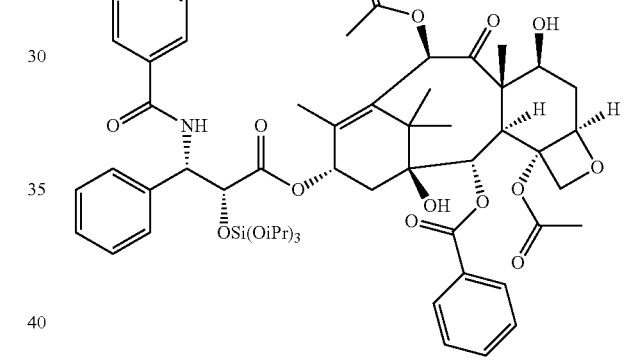
and salts thereof.
7. A compound selected from:
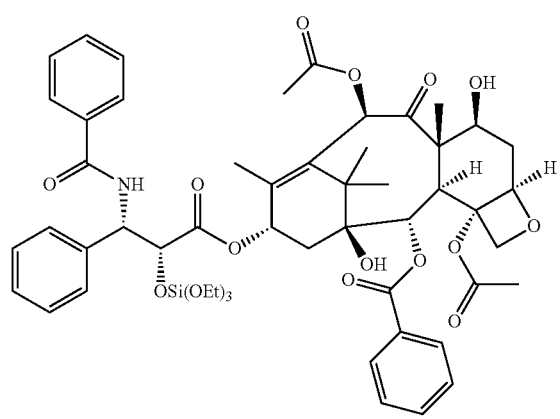
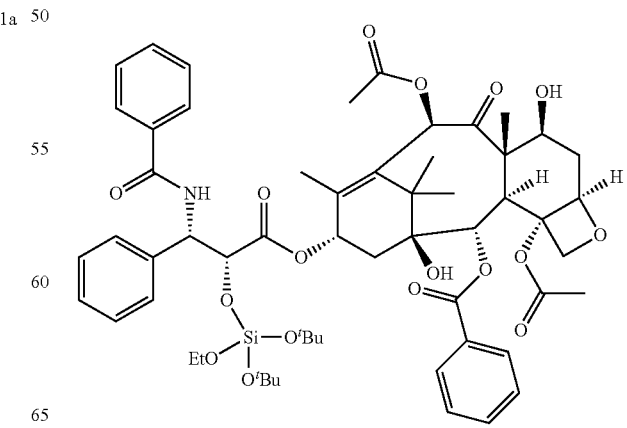

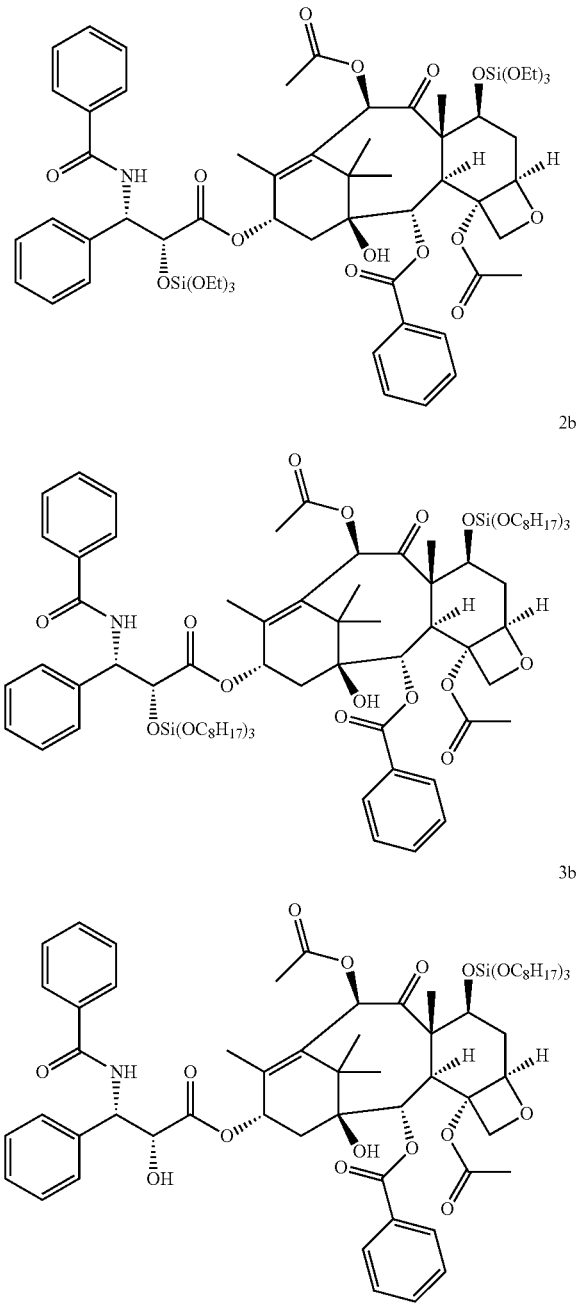

and salts thereof.

8. A composition comprising a compound as described in claim 1 and a PEG-b-PLGA block co-polymer.

9. A composition comprising a compound as described in claim 1 and a pharmaceutically acceptable carrier.

10. A nano-particle comprising a compound as described in claim 1 and a PEG-b-PLGA block co-polymer.

11. A nano-particle comprising a compound as described in claim 1 and one or more targeting moieties.

12. A method to treat cancer in an animal comprising administering to the animal a compound as described in claim 1.

13. A method to treat restenosis in an animal comprising administering to the animal a compound as described in claim 1.

14. A method to treat cancer in an animal, comprising administering to the animal a nano-particle as described in claim 10.

15. A composition comprising a compound as described in claim 3 and a PEG-b-PLGA block co-polymer.

16. A composition comprising a compound as described in claim 3 and a pharmaceutically acceptable carrier.

17. A nano-particle comprising a compound as described in claim 3 and a PEG-b-PLGA block co-polymer.

18. A nano-particle comprising a compound as described in claim 3 and one or more targeting moieties.

19. A method to treat cancer in an animal comprising administering to the animal a compound as described in claim 3.

20. A method to treat restenosis in an animal comprising administering to the animal a compound as described in claim 3.

21. A method to treat cancer in an animal, comprising administering to the animal a nano-particle as described in claim 17.

22. A composition comprising a compound as described in claim 4 and a PEG-b-PLGA block co-polymer.

23. A composition comprising a compound as described in claim 4 and a pharmaceutically acceptable carrier.

24. A nano-particle comprising a compound as described in claim 4 and a PEG-b-PLGA block co-polymer.

25. A nano-particle comprising a compound as described in claim 4 and one or more targeting moieties.

26. A method to treat cancer in an animal comprising administering to the animal a compound as described in claim 4.

27. A method to treat restenosis in an animal comprising administering to the animal a compound as described in claim 4.

28. A method to treat cancer in an animal, comprising administering to the animal a nano-particle as described in claim 4.

29. A composition comprising a compound as described in claim 5 and a PEG-b-PLGA block co-polymer.

30. A composition comprising a compound as described in claim 5 and a pharmaceutically acceptable carrier.

31. A nano-particle comprising a compound as described in claim 5 and a PEG-b-PLGA block co-polymer.

32. A nano-particle comprising a compound as described in claim 5 and one or more targeting moieties.

33. A method to treat cancer in an animal comprising administering to the animal a compound as described in claim 5.

34. A method to treat restenosis in an animal comprising administering to the animal a compound as described in claim 5.

35. A method to treat cancer in an animal, comprising administering to the animal a nano-particle as described in claim 31.

* * * * *